(12) United States Patent
Ushakov et al.

(10) Patent No.: US 11,174,432 B2
(45) Date of Patent: Nov. 16, 2021

(54) 2,3-DIHYDROBENZOTHIOPHENE DERIVATIVES

(71) Applicant: MERCK PATENT GMBH, Darmstadt (DE)

(72) Inventors: Dmitry Ushakov, Muenster (DE); Helga Haas, Lampertheim (DE); Thorsten Vom Stein, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 17 days.

(21) Appl. No.: 16/627,056

(22) PCT Filed: Jun. 25, 2018

(86) PCT No.: PCT/EP2018/066935
§ 371 (c)(1),
(2) Date: Dec. 27, 2019

(87) PCT Pub. No.: WO2019/002196
PCT Pub. Date: Jan. 3, 2019

(65) Prior Publication Data
US 2020/0123444 A1   Apr. 23, 2020

(30) Foreign Application Priority Data

Jun. 28, 2017 (EP) .................................... 17178476

(51) Int. Cl.
| | | |
|---|---|---|
| *G02F 1/1333* | (2006.01) | |
| *C09K 19/34* | (2006.01) | |
| *C07D 333/54* | (2006.01) | |
| *C07D 409/04* | (2006.01) | |

(52) U.S. Cl.
CPC ........ *C09K 19/3491* (2013.01); *C07D 333/54* (2013.01); *C07D 409/04* (2013.01)

(58) Field of Classification Search
CPC .. C09K 19/3491; C09K 19/34; C07D 333/54; C07D 409/04; G02F 1/1333
USPC .................................................... 252/299.61
See application file for complete search history.

(56) References Cited

U.S. PATENT DOCUMENTS

| | | | | |
|---|---|---|---|---|
| 4,816,473 A | * | 3/1989 | Dunn ....................... | C07C 45/68 514/443 |
| 2020/0123444 A1 | * | 4/2020 | Ushakov ............ | C09K 19/3491 |

FOREIGN PATENT DOCUMENTS

| | | |
|---|---|---|
| DE | 102004053279 A1 | 6/2005 |
| WO | 15101928 A1 | 7/2015 |

OTHER PUBLICATIONS

International Search Report wo2018ep66935 dated Sep. 26, 2018 (pp. 1-2).
D. Paul et al., A Cyclometalated Ruthenium-NHC Precatalyst for the Asymmetric Hydrogenation of (Hetero)arenes and Its Activation Pathway : Organometallics, vol. 35, 20, 2016, pp. 3641-3646.

* cited by examiner

*Primary Examiner* — Geraldina Visconti
(74) *Attorney, Agent, or Firm* — Millen, White, Zelano and Branigan, P.C.

(57) ABSTRACT

The present invention relates to 2,3-dihydrobenzothiophene derivatives of the general formula I

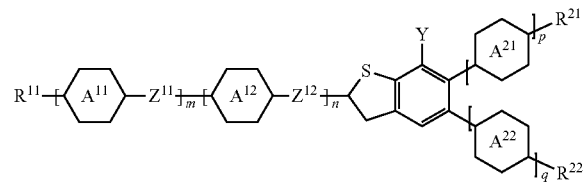

In which the occurring groups and parameters have the meanings indicated in claim 1,
to the use thereof in liquid-crystalline or mesogenic media, to liquid-crystalline or mesogenic media comprising these derivatives, and to electro-optical display elements containing these liquid-crystalline or mesogenic media.

12 Claims, No Drawings

2,3-DIHYDROBENZOTHIOPHENE DERIVATIVES

The present invention relates to 2,3-dihydrobenzothiophene derivatives, to the use thereof in liquid-crystalline or mesogenic media, to liquid-crystalline or mesogenic media comprising these derivatives, and to electro-optical display elements containing these liquid-crystalline or mesogenic media.

Liquid crystals have found widespread use since the first commercially usable liquid-crystalline compounds were found about 30 years ago. Known areas of application are, in particular, displays for watches and pocket calculators, and large display panels as used in railway stations, airports and sports arenas. Further areas of application are displays of portable computers and navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elasto-mechanical anisotropies. Depending on whether the molecules are oriented with their longitudinal axes perpendicular or parallel to the two plates of a capacitor, the latter has a different capacitance; in other words, the dielectric constant ε of the liquid-crystalline medium has different values for the two orientations. Substances whose dielectric constant is larger when the longitudinal axes of the molecules are oriented perpendicular to the capacitor plates than when they are oriented parallel are known as being dielectrically positive. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The introduction of suitable polar groups, such as, for example, nitrile groups or fluorine, into the liquid-crystal molecules enables a broad range of working voltages to be achieved.

In the case of the liquid-crystalline molecules used in conventional liquid-crystal displays, the dipole moment oriented along the longitudinal axis of the molecules is larger than the dipole moment oriented perpendicular to the longitudinal axis of the molecules. The orientation of the larger dipole moment along the longitudinal axis of the molecule also determines the orientation of the molecule in a liquid-crystal display in the field-free state. In the most widespread TN ("twisted nematic") cells, a liquid-crystalline layer with a thickness of only from about 5 to 10 µm is arranged between two flat glass plates, onto each of which an electrically conductive, transparent layer of tin oxide or indium tin oxide has been vapour-deposited as electrode. A likewise transparent alignment layer, usually consisting of a plastic (for example polyimides), is located between these films and the liquid-crystalline layer. This alignment layer serves to bring the longitudinal axes of the adjacent crystalline molecules into a preferential direction through surface forces in such a way that, in the voltage-free state, they lie uniformly on the inside of the display surface with the same alignment in a flat manner or with the same small tilt angle. Two polarisation films which only enable linear-polarised light to enter and escape are adhesively bonded to the outside of the display in a certain arrangement.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality drops drastically under certain circumstances. For greater comfort, attempts are being made to make the angle through which the display can be tilted from the viewing direction of an observer as large as possible. Attempts have recently been made to improve the viewing-angle dependence using liquid-crystalline compounds whose dipole moment perpendicular to the longitudinal axis of the molecules is larger than that parallel to the longitudinal axis of the molecule. In the field-free state, these molecules are oriented perpendicular to the glass surface of the display. In this way, it has been possible to achieve an improvement in the viewing-angle dependence. Displays of this type are known as VA-TFT ("vertically aligned") displays.

Also known are so-called IPS ("in-plane switching") displays, which contain an LC layer between two substrates with planar orientation, where the two electrodes are arranged on only one of the two substrates and preferably have interdigitated, comb-shaped structures. On application of a voltage to the electrodes an electric field with a significant component parallel to the LC layer is generated between them. This causes realignment of the LC molecules in the layer plane. Furthermore, so-called FFS ("fringe-field switching") displays have been reported (see, inter alia, S. H. Jung et al., Jpn. J. Appl. Phys., Volume 43, No. 3, 2004, 1028), which contain two electrodes on the same substrate, one of which is structured in a comb-shaped manner and the other is unstructured. A strong, so-called "fringe field" is thereby generated, i.e. a strong electric field close to the edge of the electrodes, and, throughout the cell, an electric field which has both a strong vertical component and also a strong horizontal component. FFS displays have a low viewing-angle dependence of the contrast. FFS displays usually contain an LC medium with positive dielectric anisotropy, and an alignment layer, usually of polyimide, which provides planar alignment to the molecules of the LC medium.

Another type of FFS displays has been disclosed that has a similar electrode design and layer thickness as FFS displays, but comprises a layer of an LC medium with negative dielectric anisotropy instead of an LC medium with positive dielectric anisotropy (see S. H. Lee et al., Appl. Phys. Lett. 73(20), 1998, 2882-2883 and S. H. Lee et al., Liquid Crystals 39(9), 2012, 1141-1148). The LC medium with negative dielectric anisotropy shows a more favourable director orientation that has less tilt and more twist orientation compared to the LC medium with positive dielectric anisotropy, as a result of which these displays have a higher transmission.

In DE102004053279 A1, dihydrobenzothiophene derivatives for the use in liquid crystalline media are described, for example the following compound:

FIG. 3

[Structure: C5H11-cyclohexyl-cyclohexyl-dihydrobenzothiophene with three F substituents]

However, due to their substitution pattern, the compounds described therein exhibit positive dielectric anisotropy which makes them unsuitable for the application according to the present invention.

Development in the area of liquid-crystalline materials is far from complete. In order to improve the properties of liquid-crystalline display elements, attempts are constantly being made to develop novel compounds which enable such displays to be optimised.

An object of the present invention was to provide compounds having advantageous properties for use in liquid-crystalline media.

This object is achieved in accordance with the invention by 2,3-dihydrobenzothiophene derivatives of the general formula (I)

[Structure of Formula I]

I in which
$R^{11}$, $R^{21}$ and
$R^{22}$ each, identically or differently, denote H, F, Cl, Br, I, CN, SCN, OH, $SF_5$, straight chain or branched alkyl with up to 15 C atoms which may be unsubstituted, mono- or polysubstituted by F, Cl, Br, I or CN, it being also possible for one or more non-adjacent $CH_2$ groups to be replaced, in each case independently of one another, by

[Structures of ring systems]

—O—, —S—, —NH—, —NR°—, —C(O)—, —C(O)O—, —OC(O)—, —OC(O)O—, —S—C(O)—, —CO—S—, —CH=CH— or —C≡C— in such a manner that O and/or S atoms are not linked directly to one another,
$A^{11}$, $A^{12}$
$A^{21}$ and $A^{22}$ each, independently of one another, denote a radical selected from the following groups:
a) the group consisting of trans-1,4-cyclohexylene, 1,4-cyclohexenylene, and decaline-2,6-diyl, in which one or more non-adjacent $CH_2$ groups may be replaced by —O— and/or —S— and in which one or more H atoms may be replaced by F,
b) the group consisting of 1,4-phenylene and 2,6-naphthylene, in which one or two CH groups may be replaced by N and in which, in addition, one or more H atoms may be replaced by L,
c) the group consisting of 1,3-dioxane-2,5-diyl, tetrahydrofuran-2,5-diyl, cyclobutane-1,3-diyl, thiophene-2,5-diyl, selenophene-2,5-diyl, and 1,2,3,4-tetrahydronanaphthaline-2,6-diyl, each of which may be mono- or polysubstituted by L,
d) the group consisting of bicyclo[1.1.1]pentane-1,3-diyl, bicyclo[2.2.2]octane-1,4-diyl, and spiro[3.3]heptane-2,6-diyl, in which one or more H atoms may be replaced by F L each, identically or differently, denote halogen, cyano, alkyl, alkoxy, alkylcarbonyl or alkoxycarbonyl group with 1 to 7 C atoms, wherein one or more H atoms may be substituted by F or Cl,
$Z^{11}$ and $Z^{12}$ independently of one another, denote a single bond, —$CF_2O$—, —$OCF_2$—, —$CH_2CH_2$—, —$CF_2CF_2$—, —C(O)O—, —OC(O)—, —$CH_2O$—, —$OCH_2$—, —CF—CH—, —CH=CF—, —CF—CF—, —CH=CH— or —C≡C—, preferably —$CH_2CH_2$—, —$CF_2CF_2$—, —CH=CH— or a single bond, particularly preferably a single bond.
Y denotes H, F, Cl, $CF_3$, or $OCF_3$, preferably F,
m and n are, independently of one another, 0, 1 or 2, with the proviso that at least one of m and n denotes 0.

A further object of the present invention is to provide liquid-crystalline media, in particular for use in VA, IPS or FFS displays.

This object is achieved in accordance with the invention by the provision of dihydrobenzothiophene derivatives of formula I having negative dielectric anisotropy (Δε).

In a preferred embodiment, the compounds of formula I are selected from compounds of the sub-formula Ia

[Structure of Formula Ia]

Ia wherein the occurring groups and parameters have the meanings given above and

[Structure showing $A^H$ ring]

is selected from the group consisting of trans-1,4-cyclohexylene, 1,4-cyclohexenylene, and decaline-2,6-diyl, in which one or more non-adjacent $CH_2$ groups may be replaced by —O— and/or —S— and in which one or more H atoms may be replaced by F, and preferably

has the meaning given for

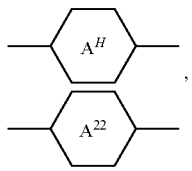 , 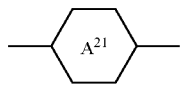 and independently of one another, are selected from the group consisting of 1,4-phenylene and 2,6-naphthylene, in which one or two CH groups may be replaced by N and in which, in addition, one or more H atoms may be replaced by F, Cl, or $CF_3$, and m, p and q independently of one another, are 0 or 1.

Preferred compounds of formula Ia are selected from the following sub-formulae:

Ia-1
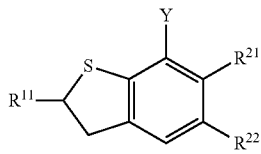

Ia-2
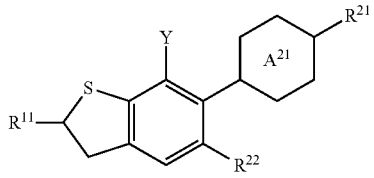

Ia-3
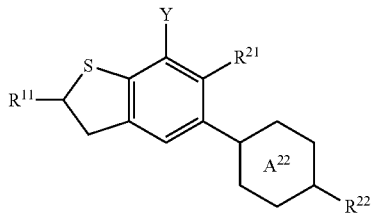

Ia-4
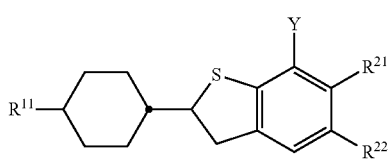

Ia-5
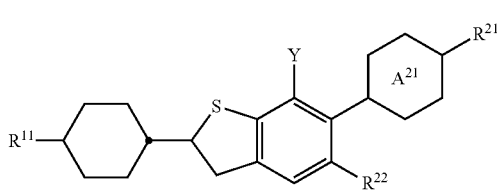

Ia-6
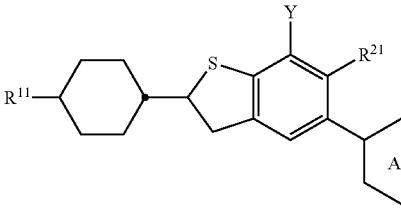

Ia-7
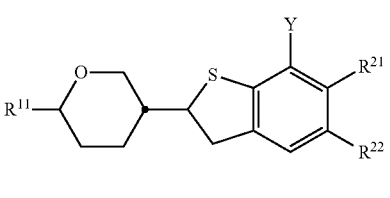

Ia-8
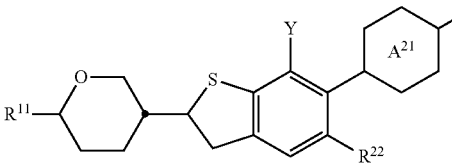

Ia-9
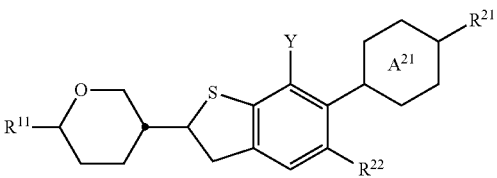

Ia-10
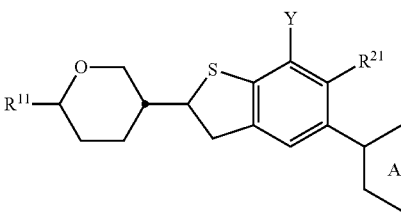

Ia-11
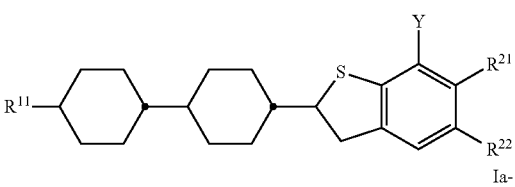

Ia-12
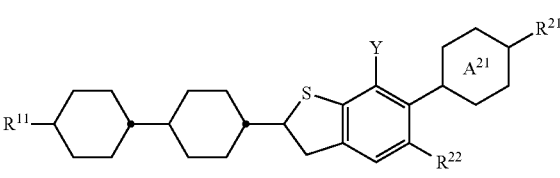

Ia-13
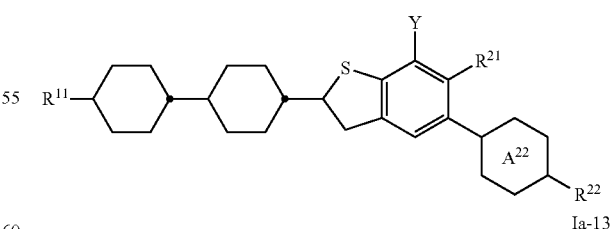

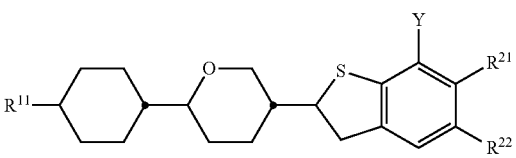

-continued

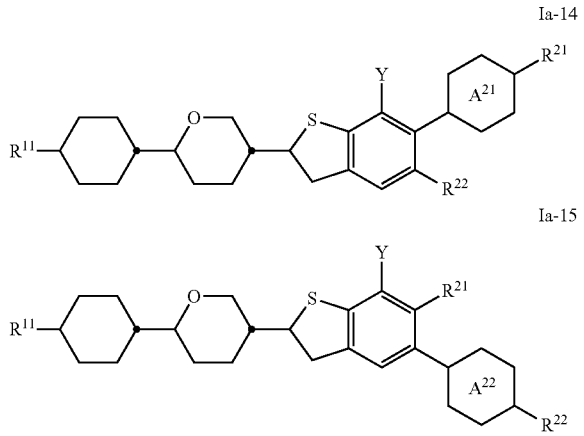

wherein $R^{11}$, $R^{21}$, $R^{22}$, Y, $A^{21}$ and $A^{22}$ have the meanings indicated above and preferably
$R^{11}$ denotes H, alkyl, alkenyl or alkoxy having up to 7 C atoms, and in which one or more H atoms may be replaced by fluorine,
$R^{21}$ and $R^{22}$ independently of one another, denote H, alkyl, alkenyl or alkoxy having up to 7 C atoms, F, Cl, CN, SCN, $SF_5$, $CF_3$, $OCF_3$, $OCF_2H$, $OCHF_2$, or —OCH=$CF_2$,
Y denotes H, Cl or F,

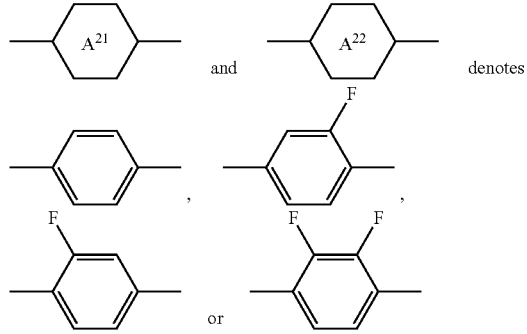

In a preferred embodiment, the compounds of formula I are selected from compounds of the sub-formula Ib

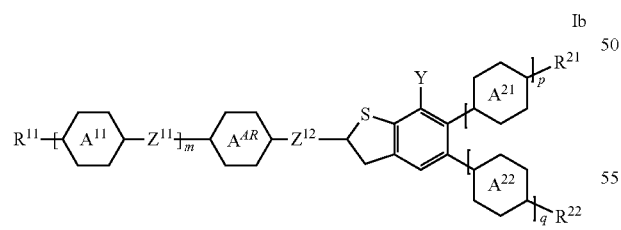

wherein the occurring groups and parameters have the meanings given above for formula I, and

is selected from the group consisting of 1,4-phenylene and 2,6-naphthylene, in which one or two CH groups may be replaced by N and in which, in addition, one or more H atoms may be replaced by F, Cl or $CF_3$, and preferably

has the meaning given for

and alternatively is selected from the group consisting of trans-1,4-cyclohexylene, 1,4-cyclohexenylene, and decaline-2,6-diyl, in which one or more non-adjacent $CH_2$ groups may be replaced by —O— and/or —S— and in which one or more H atoms may be replaced by F,

 and 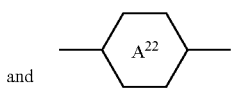

independently of one another, have the meaning given for

and
m, p and q independently of one another, are 0 or 1.
Preferred compounds of formula Ib are

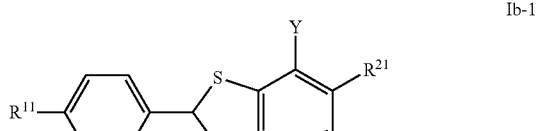

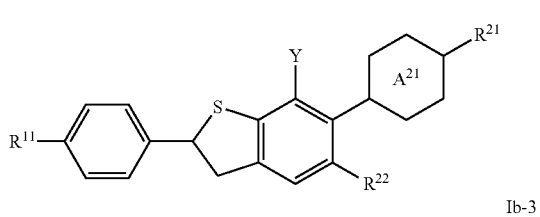

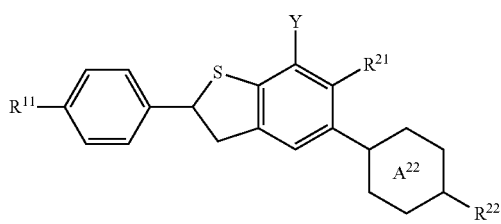

-continued
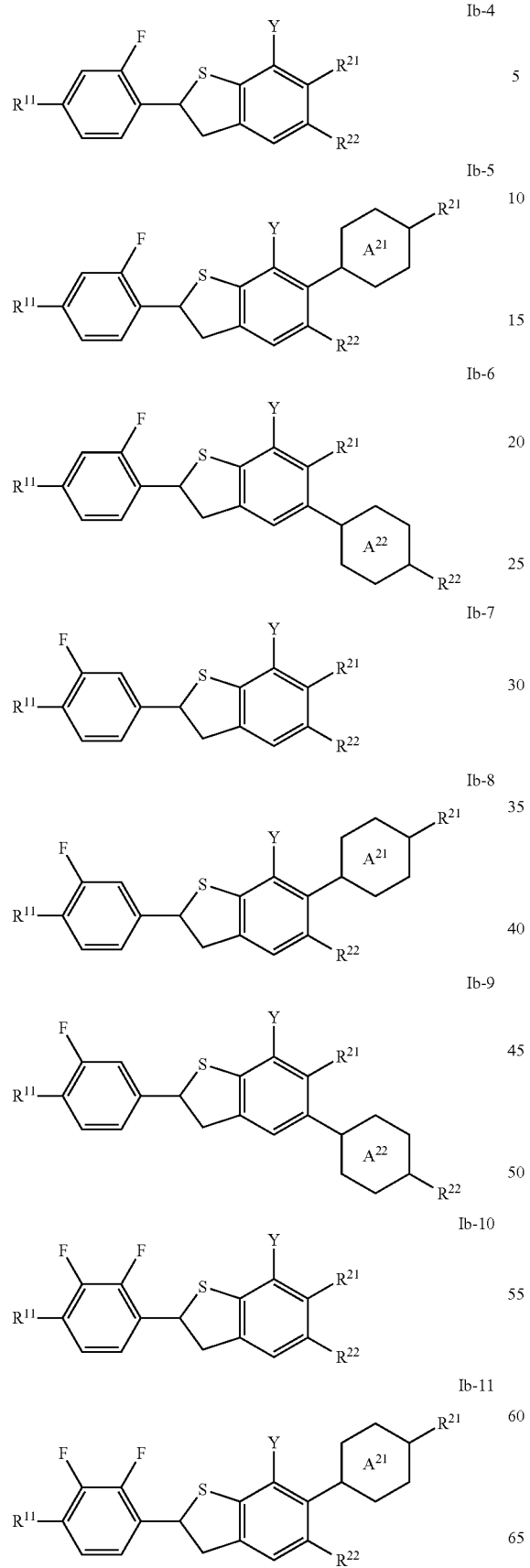
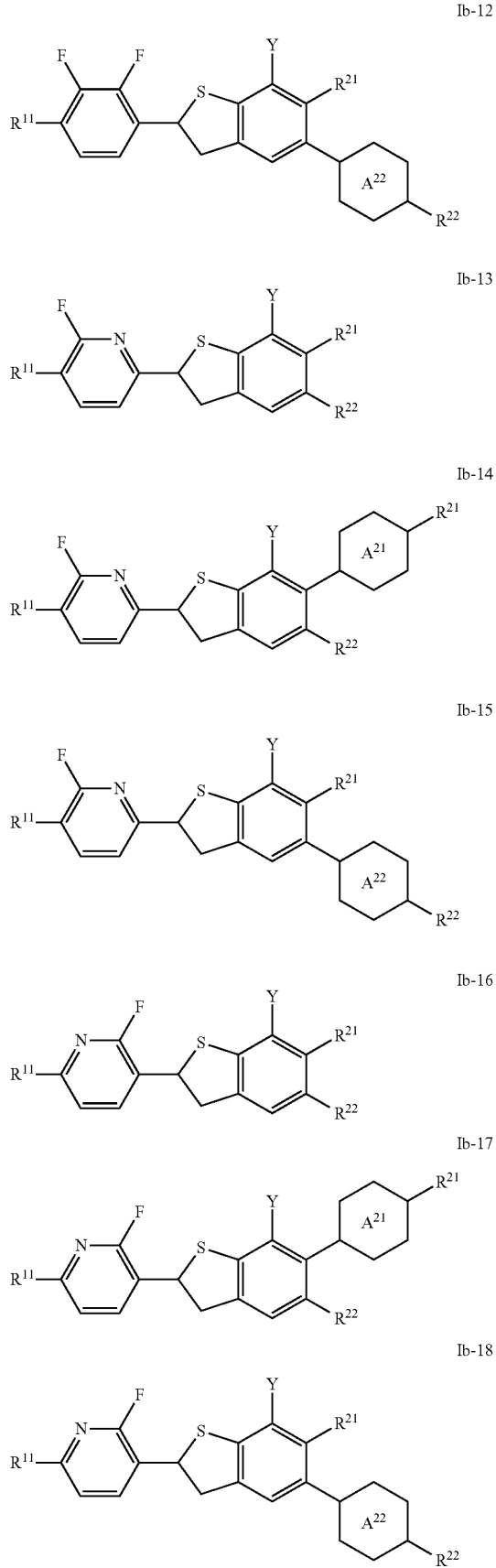

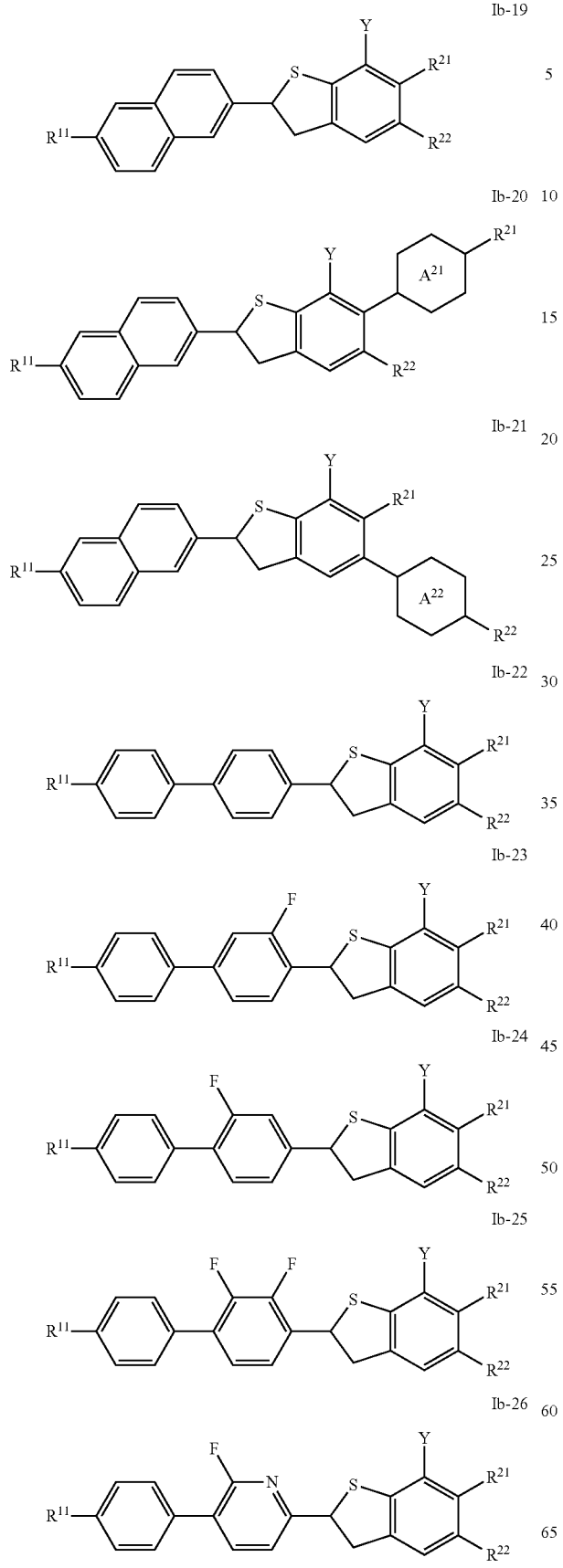
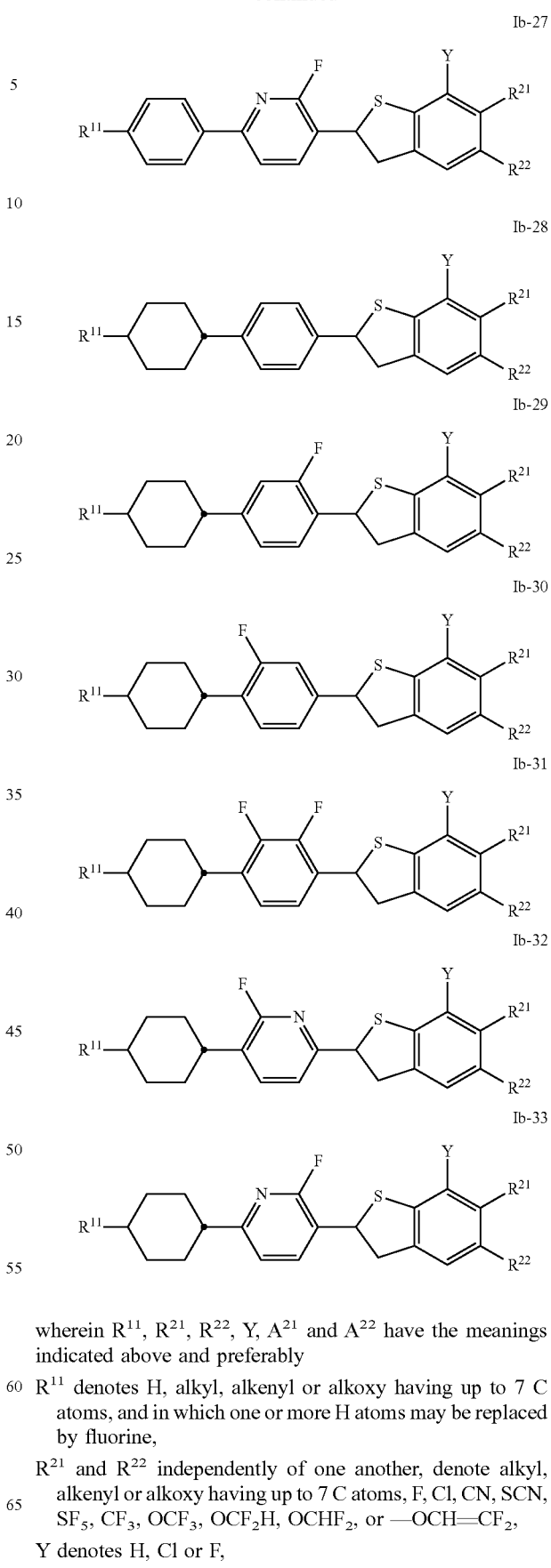

wherein $R^{11}$, $R^{21}$, $R^{22}$, Y, $A^{21}$ and $A^{22}$ have the meanings indicated above and preferably $R^{11}$ denotes H, alkyl, alkenyl or alkoxy having up to 7 C atoms, and in which one or more H atoms may be replaced by fluorine, $R^{21}$ and $R^{22}$ independently of one another, denote alkyl, alkenyl or alkoxy having up to 7 C atoms, F, Cl, CN, SCN, $SF_5$, $CF_3$, $OCF_3$, $OCF_2H$, $OCHF_2$, or —OCH=$CF_2$, Y denotes H, Cl or F,

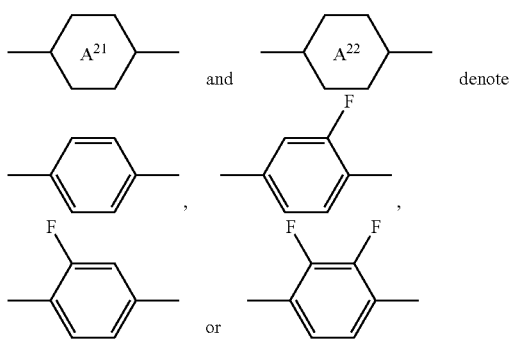

The compounds according to the invention all have negative Δε and are therefore suitable, in particular, for use in VA-TFT displays, and in IPS- and FFS displays. The compounds according to the invention preferably have a Δε of <−2.5, more preferably of <−5 and particularly preferably a Δε of <−8. They exhibit very good compatibility with the conventional substances used in liquid-crystal mixtures for displays.

For the present invention,

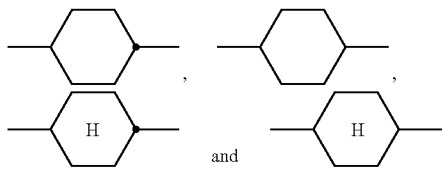

denote trans-1,4-cyclohexylene;

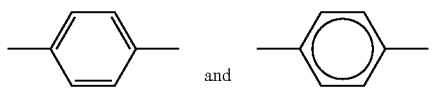

denote 1,4-phenylene.

If $R^{11}$, $R^{21}$, $R^{22}$ and L are an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

$R^{11}$, $R^{21}$, $R^{22}$ and L may each, independently of one another, be an alkenyl radical having from 2 to 15 carbon atoms, which may be straight-chain or branched. It is preferably straight-chain and has from 2 to 7 carbon atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, or hept-1-, -2-, -3-, -4-, -5- or -6-enyl.

$R^{11}$, $R^{21}$, $R^{22}$ and L may each, independently of one another, be oxaalkyl, preferably straight-chain 2-oxapropyl (=methoxymethyl), 2-oxabutyl (=ethoxymethyl) or 3-oxabutyl (=methoxyethyl), 2-, 3- or 4-oxapentyl, 2-, 3-, 4- or 5-oxahexyl, or 2-, 3-, 4-, 5- or 6-oxaheptyl.

$R^{11}$, $R^{21}$, $R^{22}$ and L may each, independently of one another, be an alkyl radical having from 1 to 15 carbon atoms in which one $CH_2$ group has been replaced by —O— and one has been replaced by —CO—, where these are preferably adjacent. This thus contains an acyloxy group —CO—O— or an oxycarbonyl group —O—CO—. This is preferably straight-chain and has from 2 to 6 carbon atoms.

$R^{11}$, $R^{21}$, $R^{22}$ and L may each, independently of one another, be an alkyl radical having from 1 to 15 carbon atoms in which one $CH_2$ group has been replaced by unsubstituted or substituted —CH=CH— and an adjacent $CH_2$ group has been replaced by CO or CO—O or O—CO, where this may be straight-chain or branched. It is preferably straight-chain and has from 4 to 13 carbon atoms.

$R^{11}$, $R^{21}$, $R^{22}$ and L may each, independently of one another, be an alkyl radical having from 1 to 15 carbon atoms or alkenyl radical having from 2 to 15 carbon atoms, each of which is monosubstituted by —CN or —$CF_3$ and is preferably straight-chain. The substitution by —CN or —$CF_3$ is possible in any desired position.

$R^{11}$, $R^{21}$, $R^{22}$ and L may each, independently of one another, be an alkyl radical in which two or more $CH_2$ groups have been replaced by —O— and/or —CO—O—, where this may be straight-chain or branched. It is preferably branched and has from 3 to 12 carbon atoms.

R, $L^2$, $L^3$, $L^4$ and $L^6$ may each, independently of one another, be an alkyl radical having from 1 to 15 carbon atoms or an alkenyl radical having from 2 to 15 carbon atoms, each of which is at least monosubstituted by halogen, where these radicals are preferably straight-chain and halogen is preferably —F or —Cl. In the case of polysubstitution, halogen is preferably —F. The resultant radicals also include perfluorinated radicals, such as —$CF_3$. In the case of monosubstitution, the fluorine or chlorine substituent can be in any desired position, but is preferably in the ω-position.

The compounds of the general formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for the said reactions. Use can be made here of variants which are known per se, but are not mentioned here in greater detail.

If desired, the starting materials can also be formed in situ by not isolating them from the reaction mixture, but instead immediately converting them further into the compounds of the general formula I Preferred synthetic pathways towards compounds according to the invention is shown in the schemes below and is further illustrated by means of the working examples. The syntheses can be adapted to the particular desired compounds of the general formula I by choice of suitable starting materials.

The compounds of formula I are preferably synthesized as shown in schemes 1 and 2.

Scheme 1

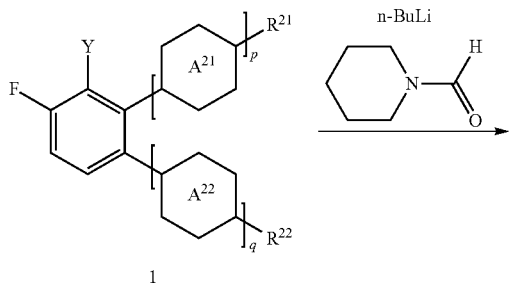

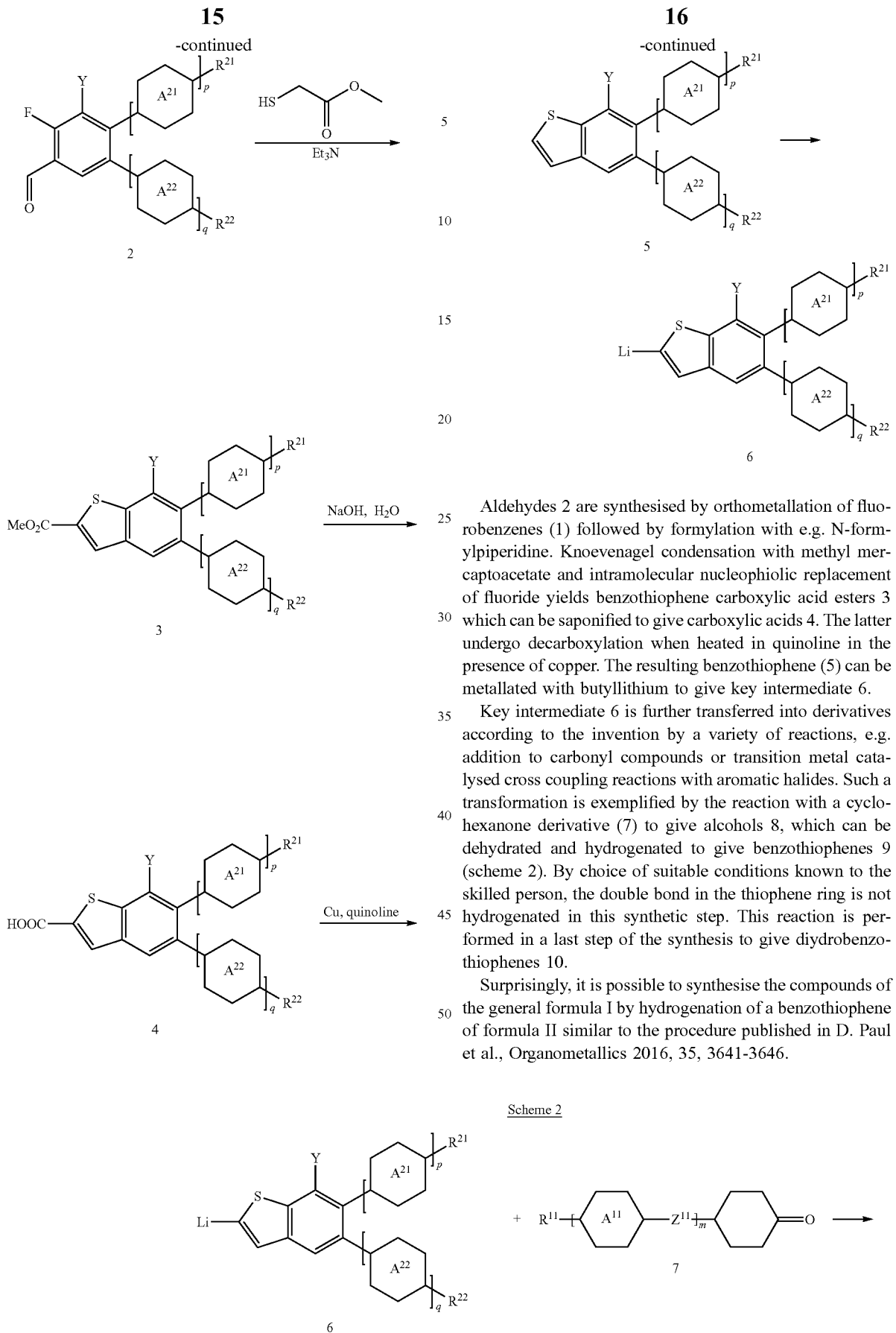

Aldehydes 2 are synthesised by orthometallation of fluorobenzenes (1) followed by formylation with e.g. N-formylpiperidine. Knoevenagel condensation with methyl mercaptoacetate and intramolecular nucleophiolic replacement of fluoride yields benzothiophene carboxylic acid esters 3 which can be saponified to give carboxylic acids 4. The latter undergo decarboxylation when heated in quinoline in the presence of copper. The resulting benzothiophene (5) can be metallated with butyllithium to give key intermediate 6.

Key intermediate 6 is further transferred into derivatives according to the invention by a variety of reactions, e.g. addition to carbonyl compounds or transition metal catalysed cross coupling reactions with aromatic halides. Such a transformation is exemplified by the reaction with a cyclohexanone derivative (7) to give alcohols 8, which can be dehydrated and hydrogenated to give benzothiophenes 9 (scheme 2). By choice of suitable conditions known to the skilled person, the double bond in the thiophene ring is not hydrogenated in this synthetic step. This reaction is performed in a last step of the synthesis to give diydrobenzothiophenes 10.

Surprisingly, it is possible to synthesise the compounds of the general formula I by hydrogenation of a benzothiophene of formula II similar to the procedure published in D. Paul et al., Organometallics 2016, 35, 3641-3646.

Scheme 2

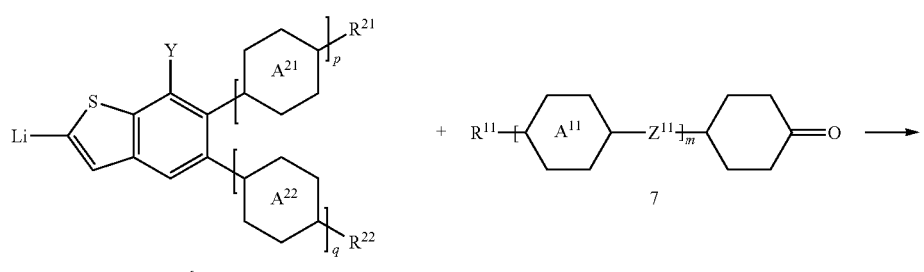

-continued

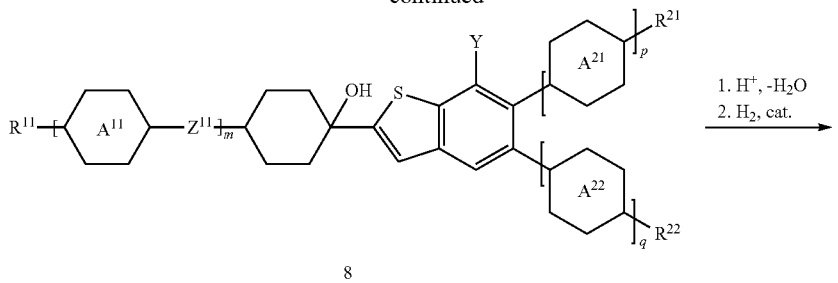
8

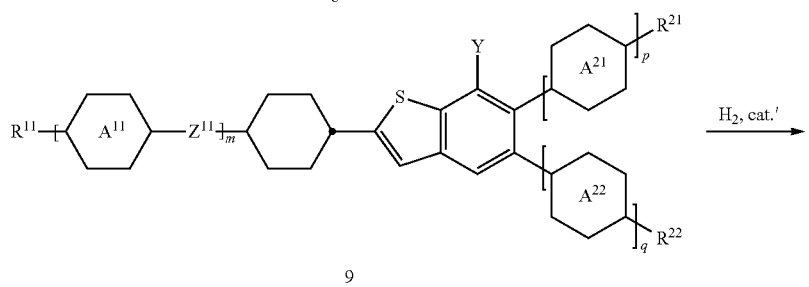
9

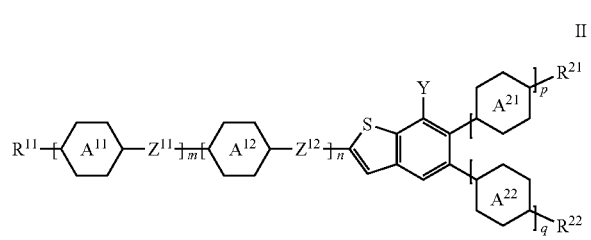
10

Another object of the present invention is a process of the preparation of a compound of formula I by hydrogenation of a compound of formula II

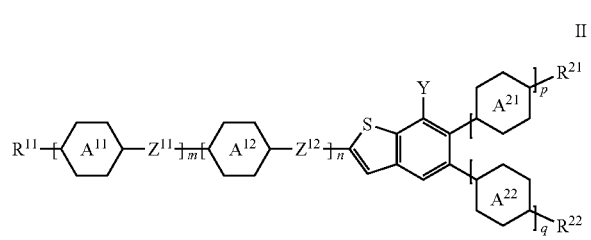

in which the occurring groups and parameters have the meanings indicated above for formula I.

The reactions described should only be regarded as illustrative. The person skilled in the art can carry out corresponding variations of the syntheses described and also follow other suitable synthetic routes in order to obtain compounds of the formula I.

As already mentioned, the compounds of the general formula I can be used in liquid-crystalline media.

The present invention therefore also relates to a liquid-crystalline medium comprising two or more liquid-crystalline compounds, comprising one or more compounds of the general formula I.

The present invention also relates to liquid-crystalline media comprising from 2 to 40, preferably from 4 to 30, components as further constituents besides one or more compounds of the formula I according to the invention.

These media particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterised by the formulae (1), (2), (3), (4) and (5):

R'-L-E-R"  (1)

R'-L-COO-E-R"  (2)

R'-L-OOC-E-R" (3)

R'-L-CH$_2$CH$_2$-E-R" (4)

R'-L-CF$_2$O-E-R" (5)

In the formulae (1), (2), (3), (4) and (5), L and E, which may be identical or different, are each, independently of one another, a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl, and G is 2-(trans-1,4-cyclohexyl)ethyl.

One of the radicals L and E is preferably Cyc or Phe. E is preferably Cyc, Phe or Phe-Cyc. The media according to the invention preferably comprise one or more components selected from the compounds of the formulae (1), (2), (3), (4) and (5) in which L and E are selected from the group consisting of Cyc and Phe and simultaneously one or more components selected from the compounds of the formulae (1), (2), (3), (4) and (5) in which one of the radicals L and E is selected from the group consisting of Cyc and Phe and the other radical is selected from the group consisting of -Phe-Phe-, -Phe-Cyc-, -Cyc-Cyc-, -G-Phe- and -G-Cyc-, and optionally one or more components selected from the compounds of the formulae (1), (2), (3), (4) and (5) in which the radicals L and E are selected from the group consisting of -Phe-Cyc-, -Cyc-Cyc-, -G-Phe- and -G-Cyc-.

In a smaller sub-group of the compounds of the formulae (1), (2), (3), (4) and (5), R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are referred to by the sub-formulae (1a), (2a), (3a), (4a) and (5a). In most of these compounds, R' and R" are different from one another, one of these radicals usually being alkyl, alkenyl, alkoxy or alkoxyalkyl.

In another smaller sub-group of the compounds of the formulae (1), (2), (3), (4) and (5), which is known as group B, E is

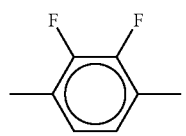

In the compounds of group B, which are referred to by the sub-formulae (1 b), (2b), (3b), (4b) and (5b), R' and R" are as defined for the compounds of the sub-formulae (1a) to (5a) and are preferably alkyl, alkenyl, alkoxy or alkoxyalkyl.

In a further smaller sub-group of the compounds of the formulae (1), (2), (3), (4) and (5), R" is —CN. This sub-group is referred to below as group C, and the compounds of this sub-group are correspondingly described by sub-formulae (1c), (2c), (3c), (4c) and (5c). In the compounds of the sub-formulae (1c), (2c), (3c), (4c) and (5c), R' is as defined for the compounds of the sub-formulae (1a) to (5a) and is preferably alkyl, alkenyl, alkoxy or alkoxyalkyl.

Besides the preferred compounds of groups A, B and C, other compounds of the formulae (1), (2), (3), (4) and (5) having other variants of the proposed substituents are also customary. All these substances are obtainable by methods which are known from the literature or analogously thereto.

Besides the compounds of the general formula I according to the invention, the media according to the invention preferably comprise one or more compounds selected from groups A, B and/or C. The proportions by weight of the compounds from these groups in the media according to the invention are:

group A: from 0 to 90%, preferably from 20 to 90%, in particular from 30 to 90%
group B: from 0 to 80%, preferably from 10 to 80%, in particular from 10 to 70%
group C: from 0 to 80%, preferably from 5 to 80%, in particular from 5 to 50%.

The media according to the invention preferably comprise from 1 to 40%, particularly preferably from 5 to 30%, of the compounds of the formula I according to the invention. Preference is furthermore given to media comprising more than 40%, in particular from 45 to 90%, of compounds of the formulae formula I according to the invention. The media preferably comprise three, four or five compounds of the formula I according to the invention.

Examples of the compounds of the formulae (1), (2), (3), (4) and (5) are the compounds listed below:

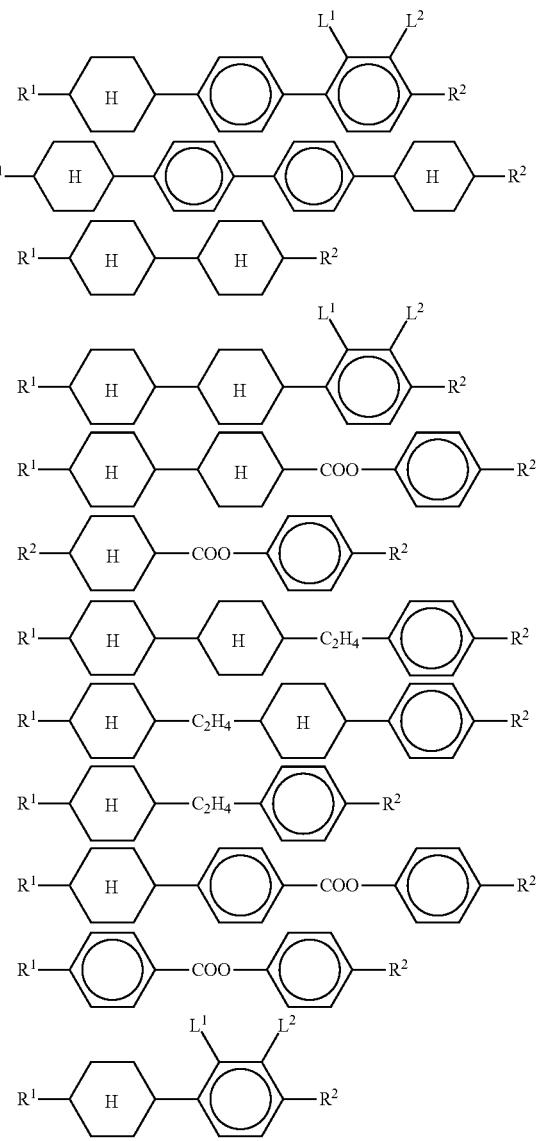

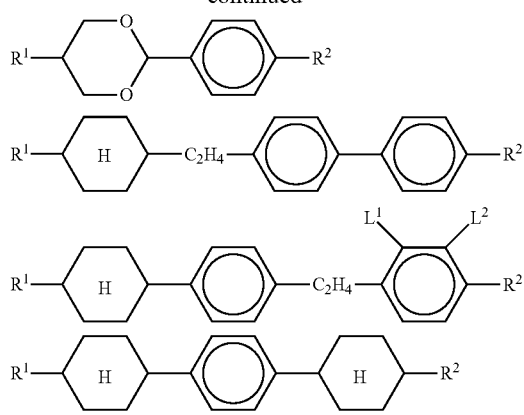
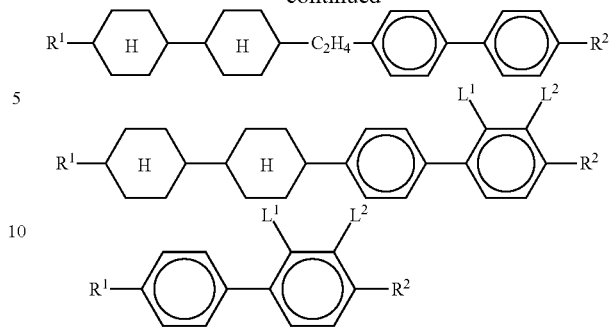
where $R^1$ and $R^2$, independently of one another, are $-C_nH_{2n+1}$ or $-OC_nH_{2n+1}$, and n=1 to 8, and $L^1$ and $L^2$, independently of one another, are —H or —F,
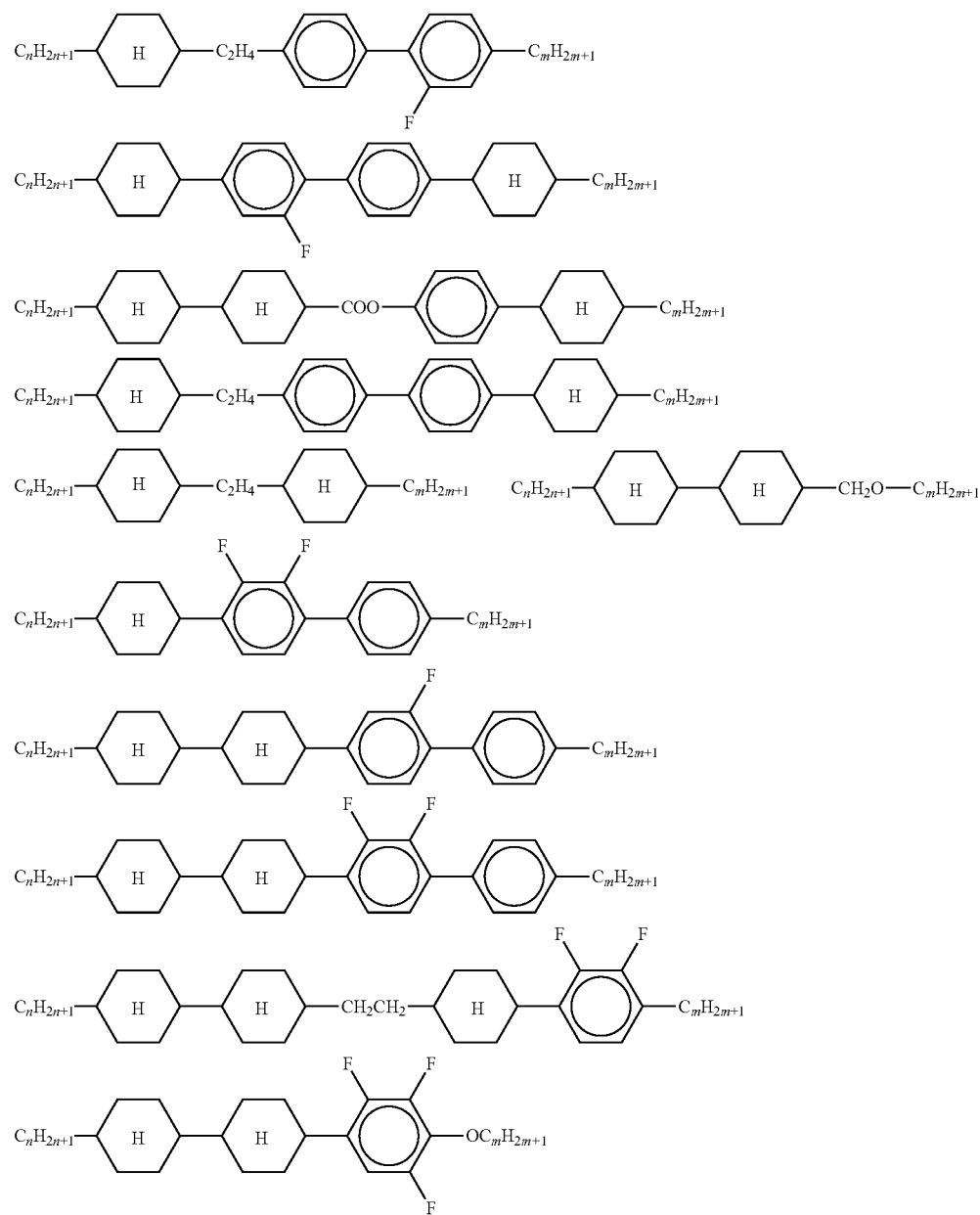

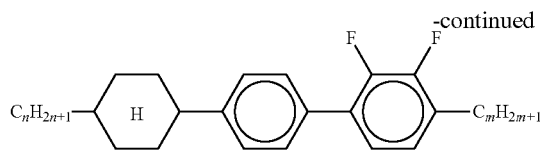

where m and n, independently of one another, are from 1 to 8.

The media according to the invention are prepared in a manner conventional per se. In general, the components are dissolved in one another, advantageously at elevated temperature. By means of suitable additives, the liquid-crystalline phases of the present invention can be modified in such a way that they can be used in all types of liquid-crystal display elements that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be used for the preparation of coloured guest-host systems or substances can be added in order to modify the dielectric anisotropy, the viscosity and/or the alignment of the nematic phases.

The present invention also relates to electro-optical liquid-crystal display elements containing a liquid-crystalline medium according to the invention.

The invention is explained in greater detail below with reference to working examples, but without being restricted thereby.

Above and below, Δn denotes the optical anisotropy (589 nm, 20° C.) and Δε denotes the dielectric anisotropy (1 kHz, 20° C.).

The Δε and Δn values of the compounds according to the invention are obtained by extrapolation from liquid-crystalline mixtures consisting of 10% of the respective compound according to the invention and 90% of the commercially available liquid-crystal mixture ZLI-2857 (for Δε) or ZLI-4792 (for Δn) (Merck KGaA, Darmstadt). In cases of limited solubility, the compound is measured in a mixture comprising only 5% of the compound, which is noted by the addition (5%) after the values in question.

ABBREVIATIONS

BuLi n-Butyllithium
THF Tetrahydrofuran
DMSO Dimethylsulfoxide
MTB ether methyl tert.-butyl ether

EXAMPLES

Example 1: 7-Fluoro-6-butoxy-2-(4-propylcyclohexyl)-2,3-dihydrobenzothiophene

Step 1:

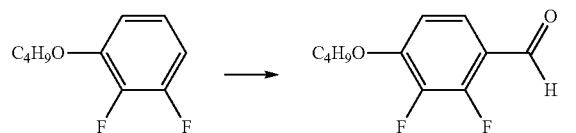

A solution of BuLi (15% in hexane, 140 mL, 0.219 mol) is added dropwise to a stirred solution of 1-butoxy-2,3-difluorobenzene (40.0 g, 0.215 mol) in THF (160 mL) at −70° C. The mixture is stirred for 30 min at the same temperature before it is treated with a solution of N-formylpiperidine (24.5 mL, 0.221 mol) in THF (80 mL). The reaction mixture is allowed to warm to −30° C., treated with water and conc. HCl (until pH 6). The aqueous phase is separated and extracted with MTB ether (2 times). The combined organic phase is washed with water, dried over $Na_2SO_4$, filtered and concentrated in vacuo. The residue was purified by flash chromatography (heptane/ethyl acetate) to give 4-butoxy-2,3-difluoro-benzaldehyde as a colorless oil Step 2:

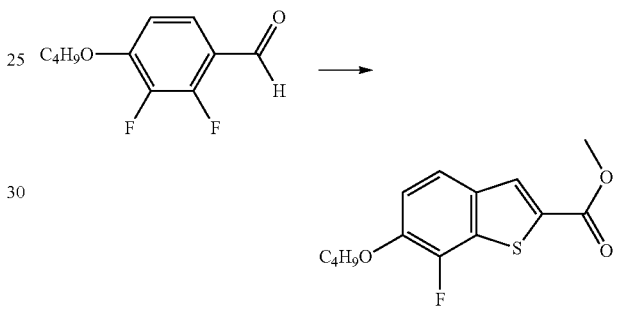

A solution of methyl mercaptoacetate (12.2 mL, 133.2 mmol) in trimethylamine (60 mL, 433.0 mmol) is added to a stirred solution of 4-butoxy-2,3-difluoro-benzaldehyde (26.0 g, 121.4 mmol) in DMSO (200 mL) at room temperature. The reaction mixture is stirred for 2 h at 80° C. before it is cooled to ambient temperature, quenched with ice water and stirred for 1 h. The precipitate is filtered off and washed with cold water to give methyl 6-butoxy-7-fluoro-benzothiophene-2-carboxylate as yellow crystals.

Step 3:

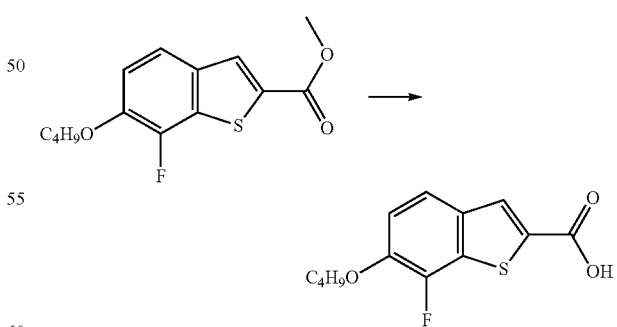

A suspension of methyl 7-fluoro-6-methyl-benzothiophene-2-carboxylate (31.0 g, 109.8 mmol) in methanol (200 mL) and THF (100 mL) is treated with NaOH solution (2 N, 150 mL, 300 mmol). The reaction mixture is stirred at 40° C. for 4 h, poured onto ice and acidified with aq. HCl (2N, until pH 3). The precipitate is filtered off and washed with water to give 6-butoxy-7-fluoro-benzothiophene-2-carboxylic acid as colourless crystals.

Step 4:

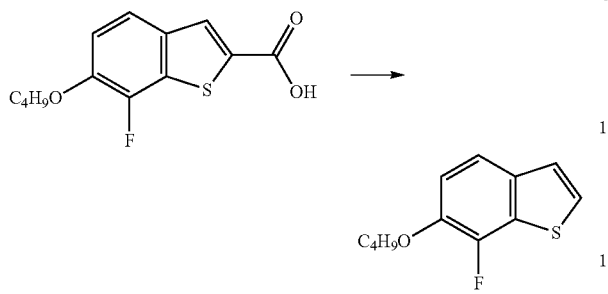

A suspension of 6-butoxy-7-fluoro-benzothiophene-2-carboxylic acid (30.0 g, 111.8 mmol) and copper powder (2.3 g, 36.9 mmol) in Quinoline (130 mL) is stirred for 2 h at 185° C. The resulted mixture is treated with 2N HCl solution (until pH 2), and extracted with ethyl acetate. The organic phase is dried over $Na_2SO_4$, filtered and concentrated under reduced pressure. The residue is filtered through a short pad of silica with n-heptane and concentrated under reduced pressure to give 6-butoxy-7-fluoro-benzothiophene as a colorless oil.

Step 5:

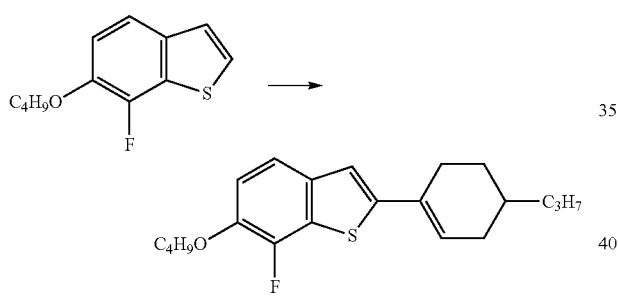

A solution of BuLi (15% in hexane, 30.8 mL, 49.0 mmol) is added dropwise to a solution of 6-butoxy-7-fluoro-benzothiophene (10.0 g, 44.5 mmol) in THF (40 mL) at −70° C. The mixture is stirred for 1 h at the same temperature before a solution of 4-propylcyclohexanone (7.5 g, 53.5 mmol) in THF (10 mL) is added. The reaction mixture is stirred for 1 h at −70° C. before it is allowed to warm to room temperature, quenched with sat. ammonium chloride solution, extracted with MTB ether, dried over $Na_2SO_4$, filtered and concentrated under reduced pressure.

The residue is purified by flash-chromatography to give the intermediate adduct as a brownish oil, which was dissolved in toluene (270 mL) and was heated under reflux in a Dean-Stark condenser in the presence of p-toluene sulfonic acid (0.6 g, 3.2 mmol). After 3 h, the reaction mixture is concentrated under reduced pressure and purified by flash chromatography to give 6-butoxy-7-fluoro-2-(4-propylcyclohexen-1-yl)benzothiophene as colourless crystals.

$^1$H NMR: 0.91 (t, J=7.1 Hz, 3H), 0.98 (t, J=7.4 Hz, 3H), 1.66-1.24 (m, 8H), 1.95-1.74 (m, 4H), 2.58-2.26 (m, 3H), 4.08 (t, J=6.5 Hz, 2H), 6.21 (dt, J=5.1, 2.4 Hz, 1H), 7.01-6.94 (m, 2H), 7.29 (dd, J=8.6, 0.8 Hz, 1H); EI-MS: 346.3

Phase sequence: K 78 SmX 79 N 100.5 I
Δε: −3.6
Δn: 0.1858
CIp.: 140° C.

Step 6:

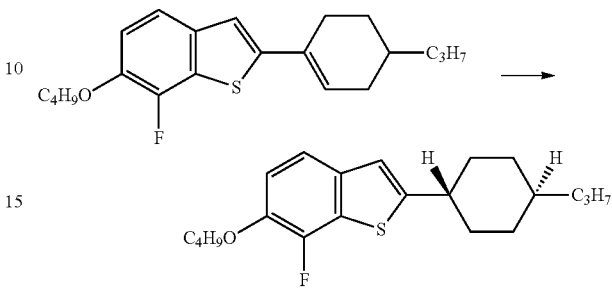

A solution of 6-butoxy-7-fluoro-2-(4-propylcyclohexen-1-yl)benzothiophene (4.0 g, 11.5 mmol) in toluene (40 mL) is catalytically hydrogenated (110° C., 147 bar) for 18 h. The reaction mixture is concentrated under reduced pressure and purified by flash chromatography, followed by crystallization from ethanol to give 6-butoxy-7-fluoro-2-(4-propylcyclohexyl)benzothiophene as colourless crystals.

$^1$H NMR: 0.84 (t, J=6.8 Hz, 3H), 0.92 (t, J=7.4 Hz, 3H), 1.30-1.18 (m, 4H), 1.62-1.38 (m, 7H), 1.90-1.69 (m, 6H), 2.98 (dtd, J=7.6, 4.9, 4.2, 2.8 Hz, 1H), 4.04 (t, J=6.6 Hz, 2H), 6.88 (dd, J=3.8, 1.3 Hz, 1H), 6.97 (dd, J=8.5, 7.6 Hz, 1H), 7.26 (dd, J=8.5, 0.8 Hz, 1H); $^{19}$F NMR: −136.5 (m, 1F); EI-MS: 348.2.

Phase sequence: K 37 N 84.9 I
Δε: −3.3
Δn: 0.1327
CIp.: 106° C.

Step 7:

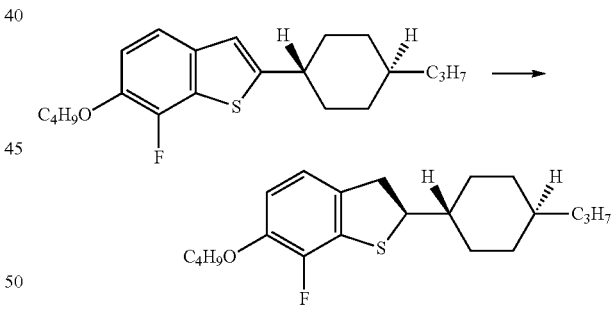

In a 35 mL Schlenk tube, equipped with a magnetic stir bar, is placed [Ru(cod)(2-methylallyl)$_2$] (24.0 mg, 0.07 mmol), 1,3-dicyclohexylimidazolium chloride (45.0 mg, 0.15 mmol) and dry potassium tert-butylate (25.1 mg, 0.22 mmol). The mixture is dissolved in toluene (20 mL) and stirred at 70° C. for 16 h under argon atmosphere. Then the solution is transferred under argon to an autoclave containing the 6-butoxy-7-fluoro-2-(4-propylcyclohexyl)-2,3-dihydrobenzothiophene (0.26 g, 0.75 mmol) and a magnetic stirring bar. The autoclave is carefully pressurized/depressurized with hydrogen gas three times before the reaction pressure of 90 bar hydrogen is adjusted. The hydrogenation is performed at 70° C. for 20 h. The reaction mixture is concentrated under reduced pressure and purified by flash chromatography (heptane/chlorobutane), followed by recrystallization from heptane to give 6-butoxy-7-fluoro-2-(4-propylcyclohexyl)-2,3-dihydrobenzothiophene as colourless crystals.

$^1$H NMR: 1.24-0.83 (m, 13H), 1.30 (h, J=7.2 Hz, 2H), 1.63-1.42 (m, 3H), 1.89-1.71 (m, 6H), 3.03 (ddd, J=15.3, 9.0, 1.2 Hz, 1H), 3.27 (dd, J=15.2, 7.7 Hz, 1H), 3.80 (dt, J=9.1, 7.8 Hz, 1H), 3.98 (t, J=6.5 Hz, 2H), 6.58 (t, J=7.9 Hz, 1H), 6.77 (dd, J=8.1, 1.1 Hz, 1H); $^{19}$F NMR: -135.0 (d, J=7.7 Hz, 1F); EI-MS: 350.2.

Phase sequence: K 84 SmA (72) I
Δε: −6.3
Δn: 0.1131
CIp: 75.4° C.

Example 2

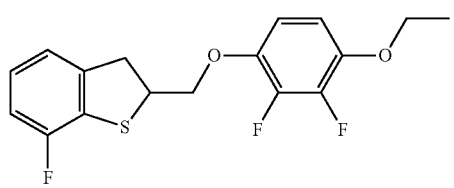 [SMILES: CCOc1ccc(OCC2Cc3cccc(F)c3S2)c(F)c1F]

Phase sequence: Tg −24 K 58 I
Δε: −3.9
Δn: 0.0349
CIp.: −170° C.
γ$_1$: 85 mPas

Example 3

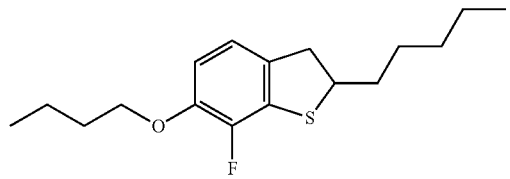 [SMILES: CCCCCC1Cc2ccc(OCCCC)c(F)c2S1]

Phase sequence: Tg −73 K 33 I
Δε: −4.6
Δn: 0.0353
CIp.: −119° C.
γ$_1$: 34 mPas

Example 4

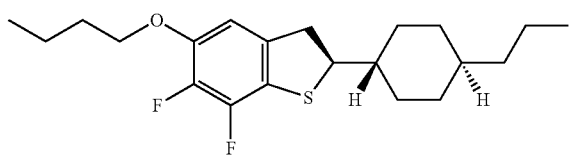 [SMILES: CCCCOc1cc2c(c(F)c1F)S[C@H]([C@H]1CC[C@H](CCC)CC1)C2]

Phase sequence: K 106 I
Δε: −6.8
Δn: 0.0651
CIp.: −25.6° C.
γ$_1$: 255 mPa s
(extrapolated from 5% in ZLI-4792 or ZLI-2857)

Example 5

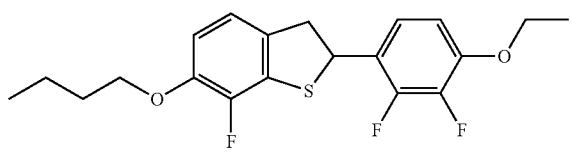 [SMILES: CCCCOc1ccc2c(c1F)SC(c1ccc(OCC)c(F)c1F)C2]

Phase sequence: K 93 I

Example 6

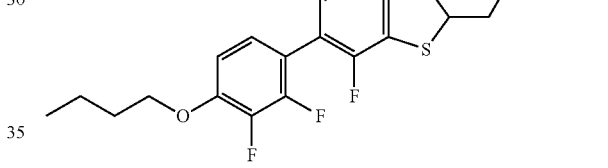

Phase sequence: K 49 I
Δε: −6.6
Δn: 0.1110
CIp.: −1.7° C.
γ$_1$: 467 mPa s
(extrapolated from 5% in ZLI-4792 or ZLI-2857)

In analogy to example 1 are obtained

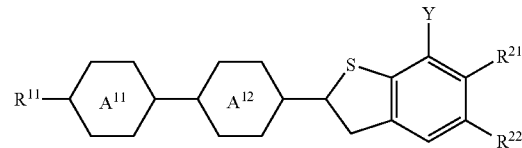

| No. | $R^{11}$ | $A^{11}$ | $A^{12}$ | Y | $R^{21}$ | $R^{22}$ |
|---|---|---|---|---|---|---|
| 1 | C$_2$H$_5$— | — | ⬡ | F | —OCH$_3$ | H |

-continued
| No. | R¹¹ | A¹¹ | A¹² | Y | R²¹ | R²² |
|---|---|---|---|---|---|---|
| 2 | C₂H₅— | — | 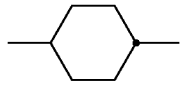 | F | —OC₂H₅ | H |
| 3 | C₂H₅— | — | 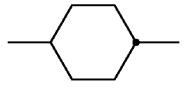 | F | —OC₃H₉ | H |
| 4 | C₂H₅— | — | 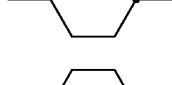 | F | —OC₄H₁₂ | H |
| 5 | C₃H₇— | — | 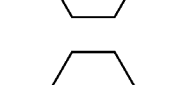 | F | —OCH₃ | H |
| 6 | C₃H₇— | — | 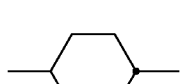 | F | —OC₂H₅ | H |
| 7 | C₃H₇— | — | 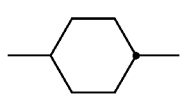 | F | —OC₃H₇ | H |
| 8 | C₃H₇— | — | 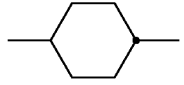 | F | —OC₄H₉ | H |
| 9 | C₄H₉— | — | 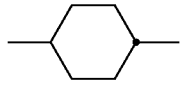 | F | —OCH₃ | H |
| 10 | C₄H₉— | — | 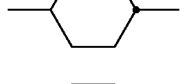 | F | —OC₂H₅ | H |
| 11 | C₄H₉— | — | 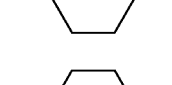 | F | —OC₃H₇ | H |
| 12 | C₄H₉— | — | 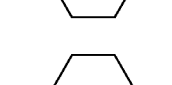 | F | —OC₄H₉ | H |
| 13 | C₅H₁₂— | — | 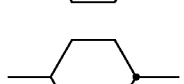 | F | —OCH₃ | H |
| 14 | C₅H₁₂— | — | 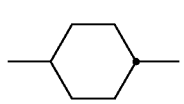 | F | —OC₂H₅ | H |
| 15 | C₅H₁₂— | — |  | F | —OC₃H₇ | H |
| 16 | C₅H₁₂— | — |  | F | —OC₄H₉ | H |

-continued
| No. | R11 | A11 | A12 | Y | R21 | R22 |
|---|---|---|---|---|---|---|
| 17 | C2H5— | — | 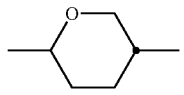 | F | —OCH3 | H |
| 18 | C2H5— | — | 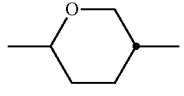 | F | —OC2H5 | H |
| 19 | C2H5— | — | 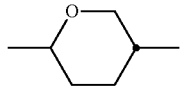 | F | —OC3H9 | H |
| 20 | C2H5— | — | 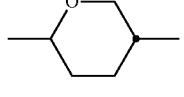 | F | —OC4H12 | H |
| 21 | C3H7— | — | 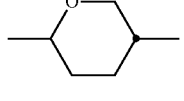 | F | —OCH3 | H |
| 22 | C3H7— | — | 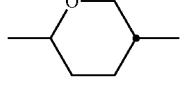 | F | —OC2H5 | H |
| 23 | C3H7— | — | 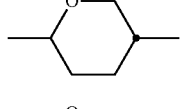 | F | —OC3H7 | H |
| 24 | C3H7— | — | 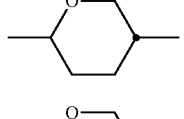 | F | —OC4H9 | H |
| 25 | C4H9— | — | 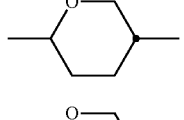 | F | —OCH3 | H |
| 26 | C4H9— | — | 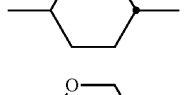 | F | —OC2H5 | H |
| 27 | C4H9— | — | 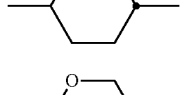 | F | —OC3H7 | H |
| 28 | C4H9— | — | 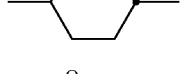 | F | —OC4H9 | H |
| 29 | C5H12— | — | 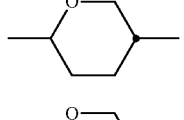 | F | —OCH3 | H |
| 30 | C5H12— | — | 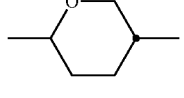 | F | —OC2H5 | H |
| 31 | C5H12— | — | 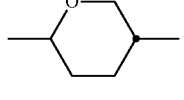 | F | —OC3H7 | H |

-continued
| No. | R$^{11}$ | A$^{11}$ | A$^{12}$ | Y | R$^{21}$ | R$^{22}$ |
|---|---|---|---|---|---|---|
| 32 | C$_5$H$_{12}$— | — | 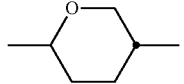 | F | —OC$_4$H$_9$ | H |
| 33 | C$_2$H$_5$— |  | 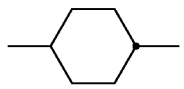 | F | —OCH$_3$ | H |
| 34 | C$_2$H$_5$— |  | 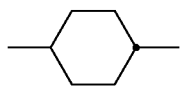 | F | —OC$_2$H$_5$ | H |
| 35 | C$_2$H$_5$— |  | 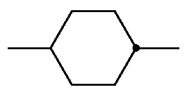 | F | —OC$_3$H$_9$ | H |
| 36 | C$_2$H$_5$— |  | 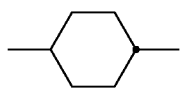 | F | —OC$_4$H$_{12}$ | H |
| 37 | C$_3$H$_7$— |  | 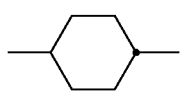 | F | —OCH$_3$ | H |
| 38 | C$_3$H$_7$— |  | 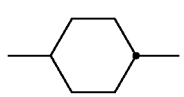 | F | —OC$_2$H$_5$ | H |
| 39 | C$_3$H$_7$— | 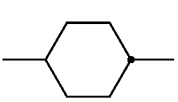 | 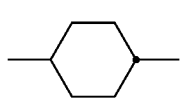 | F | —OC$_3$H$_7$ | H |
| 40 | C$_3$H$_7$— | 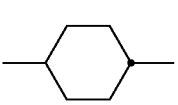 | 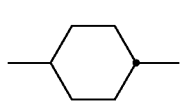 | F | —OC$_4$H$_9$ | H |
| 41 | C$_4$H$_9$— | 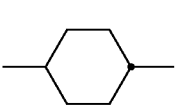 | 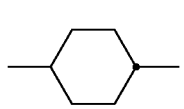 | F | —OCH$_3$ | H |
| 42 | C$_4$H$_9$— | 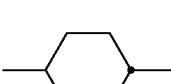 | 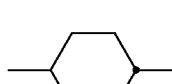 | F | —OC$_2$H$_5$ | H |
| 43 | C$_4$H$_9$— | 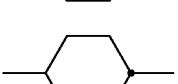 | 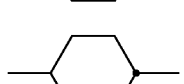 | F | —OC$_3$H$_7$ | H |
| 44 | C$_4$H$_9$— | 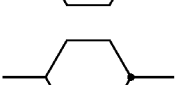 | 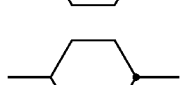 | F | —C$_4$H$_9$ | H |
| 45 | C$_5$H$_{12}$— | 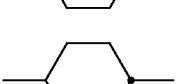 | 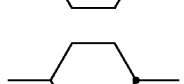 | F | —OCH$_3$ | H |
| 46 | C$_5$H$_{12}$— | 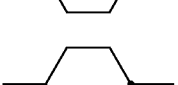 | 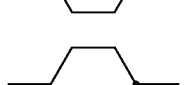 | F | —OC$_2$H$_5$ | H |

-continued
| No. | R¹¹ | A¹¹ | A¹² | Y | R²¹ | R²² |
|---|---|---|---|---|---|---|
| 47 | C₅H₁₂— |  | 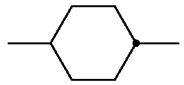 | F | —OC₃H₇ | H |
| 48 | C₅H₁₂— |  | 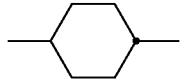 | F | —OC₄H₉ | H |
| 49 | C₂H₅— |  | 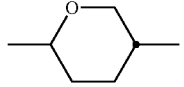 | F | —OCH₃ | H |
| 50 | C₂H₅— |  | 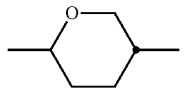 | F | —OC₂H₅ | H |
| 51 | C₂H₅— | 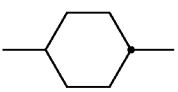 | 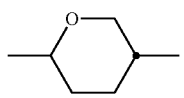 | F | —OC₃H₉ | H |
| 52 | C₂H₅— | 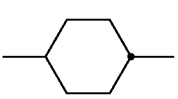 | 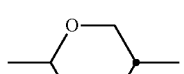 | F | —OC₄H₁₂ | H |
| 53 | C₃H₇— | 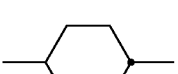 | 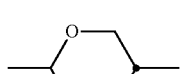 | F | —OCH₃ | H |
| 54 | C₃H₇— | 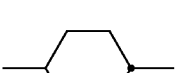 | 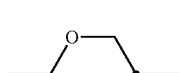 | F | —OC₂H₅ | H |
| 55 | C₃H₇— |  | 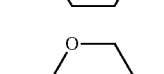 | F | —OC₃H₇ | H |
| 56 | C₃H₇— | 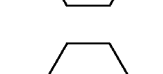 | 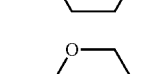 | F | —OC₄H₉ | H |
| 57 | C₄H₉— | 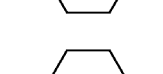 | 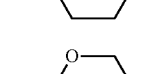 | F | —OCH₃ | H |
| 58 | C₄H₉— | 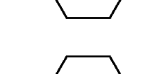 | 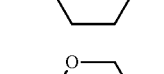 | F | —OC₂H₅ | H |
| 59 | C₄H₉— | 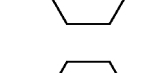 | 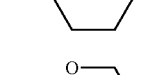 | F | —OC₃H₇ | H |
| 60 | C₄H₉— | 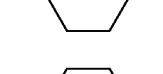 | 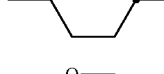 | F | —OC₄H₉ | H |
| 61 | C₅H₁₂— | 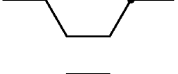 | 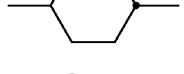 | F | —OCH₃ | H |

-continued
| No. | R$^{11}$ | A$^{11}$ | A$^{12}$ | Y | R$^{21}$ | R$^{22}$ |
|---|---|---|---|---|---|---|
| 62 | C$_5$H$_{12}$— |  | 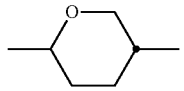 | F | —OC$_2$H$_5$ | H |
| 63 | C$_5$H$_{12}$— |  | 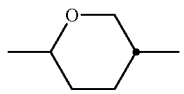 | F | —OC$_3$H$_7$ | H |
| 64 | C$_5$H$_{12}$— |  | 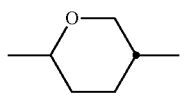 | F | —OC$_4$H$_9$ | H |
| 65 | C$_2$H$_5$— | — | 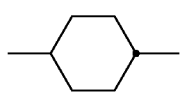 | F | F | H |
| 66 | C$_2$H$_5$— | — | 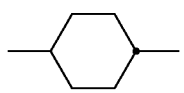 | F | F | F |
| 67 | C$_2$H$_5$— | — | 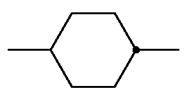 | F | F | —CH$_3$ |
| 68 | C$_2$H$_5$— | — | 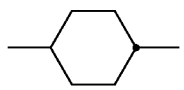 | F | F | —C$_2$H$_5$ |
| 69 | C$_2$H$_5$— | — | 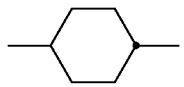 | F | F | —C$_3$H$_7$ |
| 70 | C$_2$H$_5$— | — |  | F | F | —OCH$_3$ |
| 71 | C$_2$H$_5$— | — |  | F | F | —OC$_2$H$_5$ |
| 72 | C$_2$H$_5$— | — |  | F | F | —OC$_3$H$_7$ |
| 73 | C$_2$H$_5$— | — |  | F | F | —OC$_4$H$_9$ |
| 74 | C$_3$H$_7$— | — |  | F | F | H |
| 75 | C$_3$H$_7$— | — |  | F | F | F |
| 76 | C$_3$H$_7$— | — |  | F | F | —CH$_3$ |
| 77 | C$_3$H$_7$— | — |  | F | F | —C$_2$H$_5$ |

-continued
| No. | R$^{11}$ | A$^{11}$ | A$^{12}$ | Y | R$^{21}$ | R$^{22}$ |
|---|---|---|---|---|---|---|
| 78 | C$_3$H$_7$— | — | 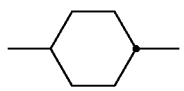 | F | F | —C$_3$H$_7$ |
| 79 | C$_3$H$_7$— | — | 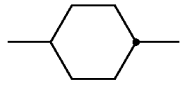 | F | F | —OCH$_3$ |
| 80 | C$_3$H$_7$— | — | 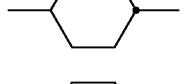 | F | F | —OC$_2$H$_5$ |
| 81 | C$_3$H$_7$— | — | 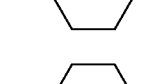 | F | F | —OC$_3$H$_7$ |
| 82 | C$_3$H$_7$— | — | 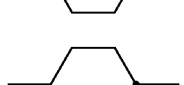 | F | F | —OC$_4$H$_9$ |
| 83 | C$_4$H$_9$— | — | 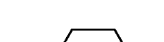 | F | F | H |
| 84 | C$_4$H$_9$— | — | 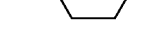 | F | F | F |
| 85 | C$_4$H$_9$— | — |  | F | F | —CH$_3$ |
| 86 | C$_4$H$_9$— | — |  | F | F | —C$_2$H$_5$ |
| 87 | C$_4$H$_9$— | — | 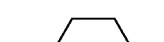 | F | F | —C$_3$H$_7$ |
| 88 | C$_4$H$_9$— | — | 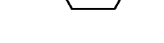 | F | F | —OCH$_3$ |
| 89 | C$_4$H$_9$— | — |  | F | F | —OC$_2$H$_5$ |
| 90 | C$_4$H$_9$— | — |  | F | F | —OC$_3$H$_7$ |
| 91 | C$_4$H$_9$— | — | 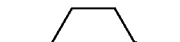 | F | F | —OC$_4$H$_9$ |
| 92 | C$_5$H$_{12}$— | — | 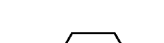 | F | F | H |

-continued
| No. | R¹¹ | A¹¹ | A¹² | Y | R²¹ | R²² |
|---|---|---|---|---|---|---|
| 93 | C₅H₁₂— | — | 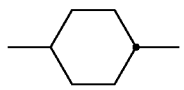 | F | F | F |
| 94 | C₅H₁₂— | — | 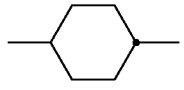 | F | F | —CH₃ |
| 95 | C₅H₁₂— | — |  | F | F | —C₂H₅ |
| 96 | C₅H₁₂— | — | 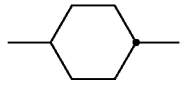 | F | F | —C₃H₇ |
| 97 | C₅H₁₂— | — |  | F | F | —OCH₃ |
| 98 | C₅H₁₂— | — | 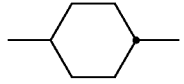 | F | F | —OC₂H₅ |
| 99 | C₅H₁₂— | — |  | F | F | —OC₃H₇ |
| 100 | C₅H₁₂— | — | 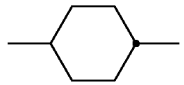 | F | F | —OC₄H₉ |
| 101 | C₂H₅— | — | 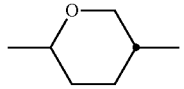 | F | F | H |
| 102 | C₂H₅— | — | 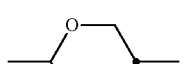 | F | F | F |
| 103 | C₂H₅— | — | 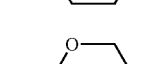 | F | F | —CH₃ |
| 104 | C₂H₅— | — | 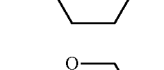 | F | F | —C₂H₅ |
| 105 | C₂H₅— | — | 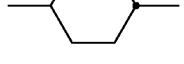 | F | F | —C₃H₇ |
| 106 | C₂H₅— | — | 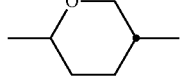 | F | F | —OCH₃ |
| 107 | C₂H₅— | — | 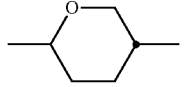 | F | F | —OC₂H₅ |

-continued
| No. | R¹¹ | A¹¹ | A¹² | Y | R²¹ | R²² |
|---|---|---|---|---|---|---|
| 108 | C₂H₅— | — | 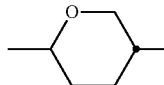 | F | F | —OC₃H₇ |
| 109 | C₂H₅— | — | 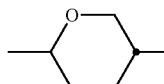 | F | F | —OC₄H₉ |
| 110 | C₃H₇— | — | 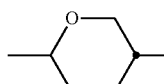 | F | F | H |
| 111 | C₃H₇— | — | 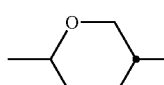 | F | F | F |
| 112 | C₃H₇— | — | 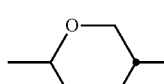 | F | F | —CH₃ |
| 113 | C₃H₇— | — | 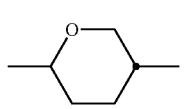 | F | F | —C₂H₅ |
| 114 | C₃H₇— | — | 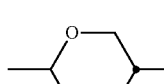 | F | F | —C₃H₇ |
| 115 | C₃H₇— | — | 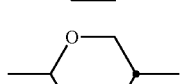 | F | F | —OCH₃ |
| 116 | C₃H₇— | — | 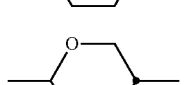 | F | F | —OC₂H₅ |
| 117 | C₃H₇— | — | 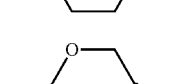 | F | F | —OC₃H₇ |
| 118 | C₃H₇— | — | 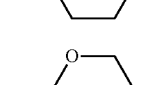 | F | F | —OC₄H₉ |
| 119 | C₄H₉— | — | 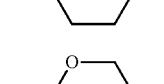 | F | F | H |
| 120 | C₄H₉— | — | 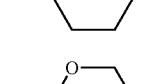 | F | F | F |
| 121 | C₄H₉— | — | 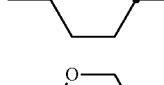 | F | F | —CH₃ |
| 122 | C₄H₉— | — | 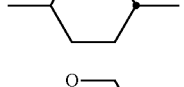 | F | F | —C₂H₅ |

-continued
| No. | $R^{11}$ | $A^{11}$ | $A^{12}$ | Y | $R^{21}$ | $R^{22}$ |
|---|---|---|---|---|---|---|
| 123 | $C_4H_9-$ | — | 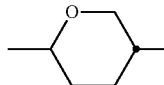 | F | F | $-C_3H_7$ |
| 124 | $C_4H_9-$ | — | 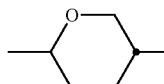 | F | F | $-OCH_3$ |
| 125 | $C_4H_9-$ | — | 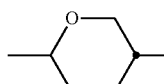 | F | F | $-OC_2H_5$ |
| 126 | $C_4H_9-$ | — | 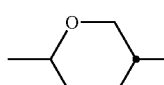 | F | F | $-OC_3H_7$ |
| 127 | $C_4H_9-$ | — | 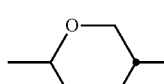 | F | F | $-OC_4H_9$ |
| 128 | $C_5H_{12}-$ | — | 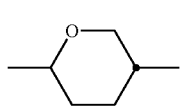 | F | F | H |
| 129 | $C_5H_{12}-$ | — | 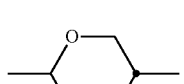 | F | F | F |
| 130 | $C_5H_{12}-$ | — | 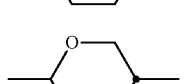 | F | F | $-CH_3$ |
| 131 | $C_5H_{12}-$ | — | 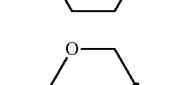 | F | F | $-C_2H_5$ |
| 132 | $C_5H_{12}-$ | — | 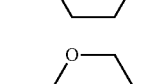 | F | F | $-C_3H_7$ |
| 133 | $C_5H_{12}-$ | — | 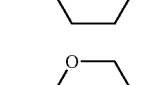 | F | F | $-OCH_3$ |
| 134 | $C_5H_{12}-$ | — | 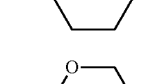 | F | F | $-OC_2H_5$ |
| 135 | $C_5H_{12}-$ | — | 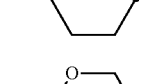 | F | F | $-OC_3H_7$ |
| 136 | $C_5H_{12}-$ | — | 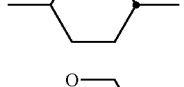 | F | F | $-OC_4H_9$ |
| 137 | $C_2H_5-$ | 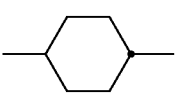 | 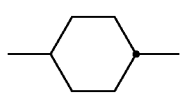 | F | F | H |

-continued
| No. | R¹¹ | A¹¹ | A¹² | Y | R²¹ | R²² |
|---|---|---|---|---|---|---|
| 138 | C₂H₅— | 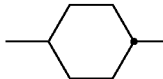 | 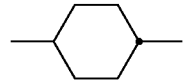 | F | F | F |
| 139 | C₂H₅— | 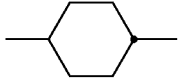 | 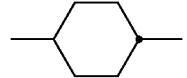 | F | F | —CH₃ |
| 140 | C₂H₅— | 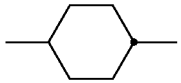 | 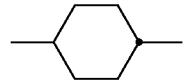 | F | F | —C₂H₅ |
| 141 | C₂H₅— | 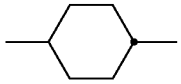 |  | F | F | —C₃H₇ |
| 142 | C₂H₅— | 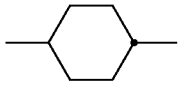 | 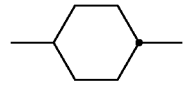 | F | F | —OCH₃ |
| 143 | C₂H₅— | 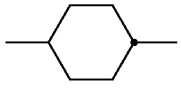 | 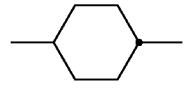 | F | F | —OC₂H₅ |
| 144 | C₂H₅— | 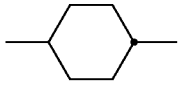 | 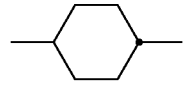 | F | F | —OC₃H₇ |
| 145 | C₂H₅— | 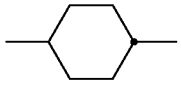 | 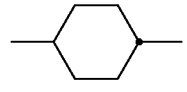 | F | F | —OC₄H₉ |
| 146 | C₃H₇— | 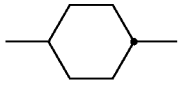 | 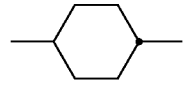 | F | F | H |
| 147 | C₃H₇— | 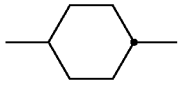 | 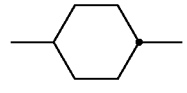 | F | F | F |
| 148 | C₃H₇— | 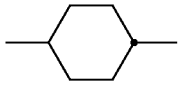 | 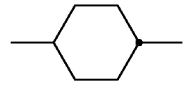 | F | F | —CH₃ |
| 149 | C₃H₇— | 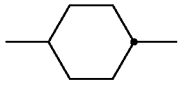 | 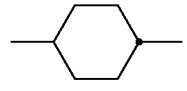 | F | F | —C₂H₅ |
| 150 | C₃H₇— | 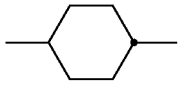 | 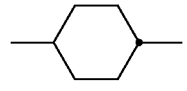 | F | F | —C₃H₇ |
| 151 | C₃H₇— | 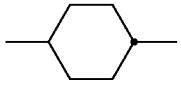 |  | F | F | —OCH₃ |
| 152 | C₃H₇— | 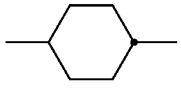 |  | F | F | —OC₂H₅ |
| 153 | C₃H₇— | 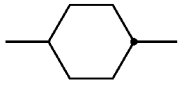 | 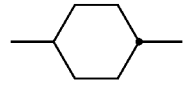 | F | F | —OC₃H₇ |

-continued
| No. | R11 | A11 | A12 | Y | R21 | R22 |
|---|---|---|---|---|---|---|
| 154 | C3H7— |  |  | F | F | —OC4H9 |
| 155 | C4H9— |  | 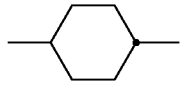 | F | F | H |
| 156 | C4H9— | 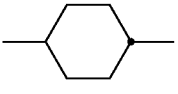 | 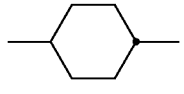 | F | F | F |
| 157 | C4H9— | 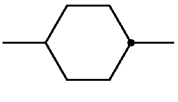 | 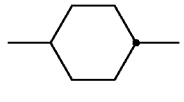 | F | F | —CH3 |
| 158 | C4H9— | 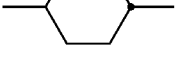 | 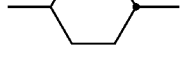 | F | F | —C2H5 |
| 159 | C4H9— | 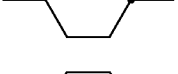 | 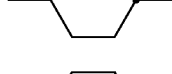 | F | F | —C3H7 |
| 160 | C4H9— | 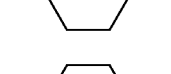 | 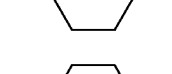 | F | F | —OCH3 |
| 161 | C4H9— | 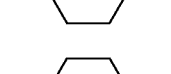 | 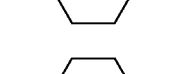 | F | F | —OC2H5 |
| 162 | C4H9— | 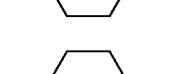 | 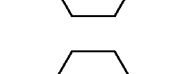 | F | F | —OC3H7 |
| 163 | C4H9— | 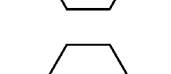 | 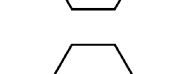 | F | F | —OC4H9 |
| 164 | C5H12— | 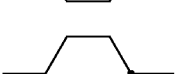 |  | F | F | H |
| 165 | C5H12— | 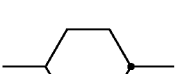 | 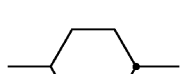 | F | F | F |
| 166 | C5H12— | 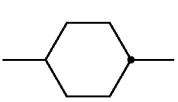 | 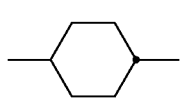 | F | F | —CH3 |
| 167 | C5H12— |  | 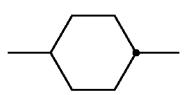 | F | F | —C2H5 |
| 168 | C5H12— |  |  | F | F | —C3H7 |

-continued
| No. | R¹¹ | A¹¹ | A¹² | Y | R²¹ | R²² |
|---|---|---|---|---|---|---|
| 169 | C₅H₁₂— | 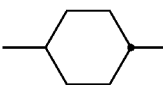 | 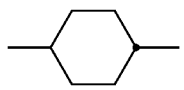 | F | F | —OCH₃ |
| 170 | C₅H₁₂— | 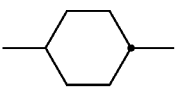 | 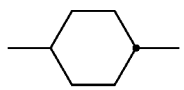 | F | F | —OC₂H₅ |
| 171 | C₅H₁₂— | 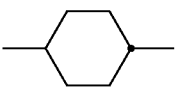 | 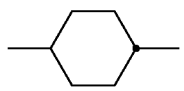 | F | F | —OC₃H₇ |
| 172 | C₅H₁₂— | 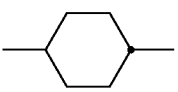 | 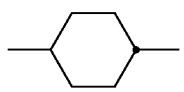 | F | F | —OC₄H₉ |
| 173 | C₂H₅— | 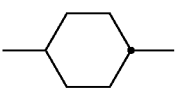 | 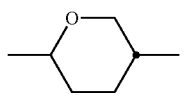 | F | F | H |
| 174 | C₂H₅— | 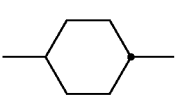 | 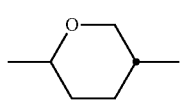 | F | F | F |
| 175 | C₂H₅— | 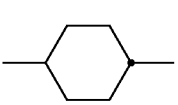 | 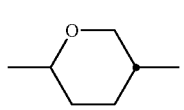 | F | F | —CH₃ |
| 176 | C₂H₅— | 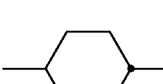 | 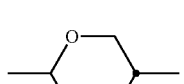 | F | F | —C₂H₅ |
| 177 | C₂H₅— | 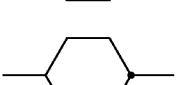 | 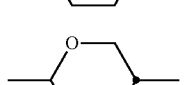 | F | F | —C₃H₇ |
| 178 | C₂H₅— | 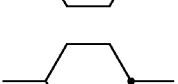 | 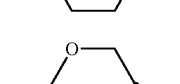 | F | F | —OCH₃ |
| 179 | C₂H₅— | 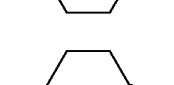 | 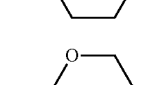 | F | F | —OC₂H₅ |
| 180 | C₂H₅— | 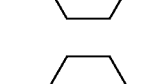 | 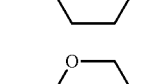 | F | F | —OC₃H₇ |
| 181 | C₂H₅— |  | 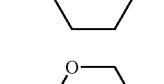 | F | F | —OC₄H₉ |
| 182 | C₃H₇— | 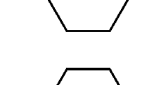 | 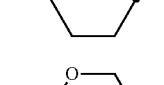 | F | F | H |
| 183 | C₃H₇— | 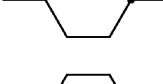 | 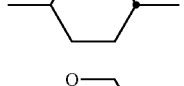 | F | F | F |

-continued
| No. | R[11] | A[11] | A[12] | Y | R[21] | R[22] |
|---|---|---|---|---|---|---|
| 184 | C$_3$H$_7$— | 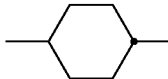 | 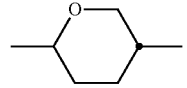 | F | F | —CH$_3$ |
| 185 | C$_3$H$_7$— |  | 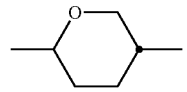 | F | F | —C$_2$H$_5$ |
| 186 | C$_3$H$_7$— | 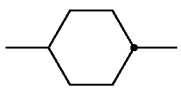 | 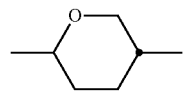 | F | F | —C$_3$H$_7$ |
| 187 | C$_3$H$_7$— | 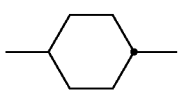 | 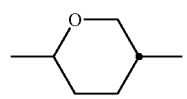 | F | F | —OCH$_3$ |
| 188 | C$_3$H$_7$— | 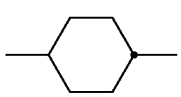 | 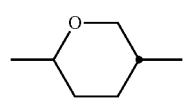 | F | F | —OC$_2$H$_5$ |
| 189 | C$_3$H$_7$— | 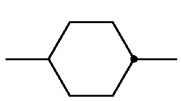 | 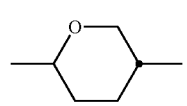 | F | F | —OC$_3$H$_7$ |
| 190 | C$_3$H$_7$— | 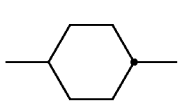 | 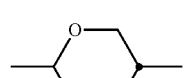 | F | F | —OC$_4$H$_9$ |
| 191 | C$_4$H$_9$— | 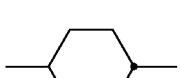 | 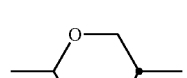 | F | F | H |
| 192 | C$_4$H$_9$— | 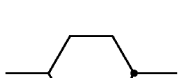 | 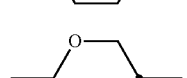 | F | F | F |
| 193 | C$_4$H$_9$— | 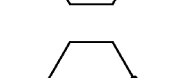 | 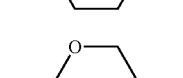 | F | F | —CH$_3$ |
| 194 | C$_4$H$_9$— | 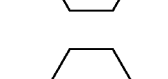 | 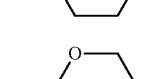 | F | F | —C$_2$H$_5$ |
| 195 | C$_4$H$_9$— | 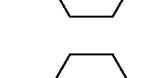 | 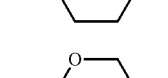 | F | F | —C$_3$H$_7$ |
| 196 | C$_4$H$_9$— | 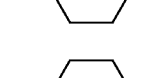 | 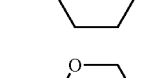 | F | F | —OCH$_3$ |
| 197 | C$_4$H$_9$— | 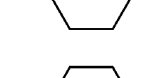 | 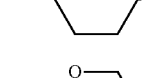 | F | F | —OC$_2$H$_5$ |
| 198 | C$_4$H$_9$— | 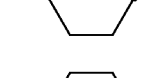 | 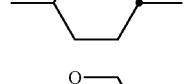 | F | F | —OC$_3$H$_7$ |

-continued
| No. | R¹¹ | A¹¹ | A¹² | Y | R²¹ | R²² |
|---|---|---|---|---|---|---|
| 199 | C₄H₉— | 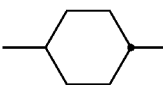 | 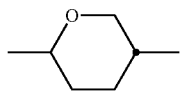 | F | F | —OC₄H₉ |
| 200 | C₅H₁₂— | 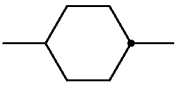 | 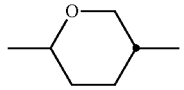 | F | F | H |
| 201 | C₅H₁₂— |  | 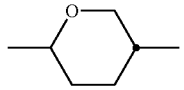 | F | F | F |
| 202 | C₅H₁₂— | 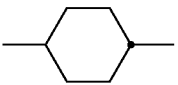 | 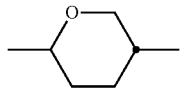 | F | F | —CH₃ |
| 203 | C₅H₁₂— | 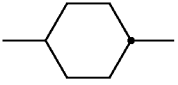 | 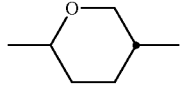 | F | F | —C₂H₅ |
| 204 | C₅H₁₂— | 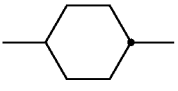 | 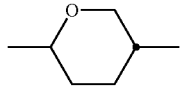 | F | F | —C₃H₇ |
| 205 | C₅H₁₂— | 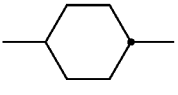 | 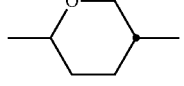 | F | F | —OCH₃ |
| 206 | C₅H₁₂— | 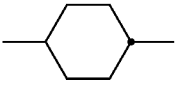 | 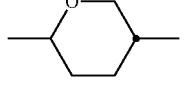 | F | F | —OC₂H₅ |
| 207 | C₅H₁₂— | 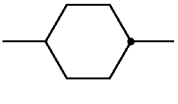 | 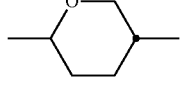 | F | F | —OC₃H₇ |
| 208 | C₅H₁₂— | 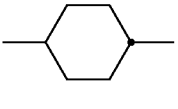 | 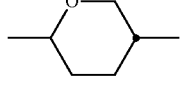 | F | F | —OC₄H₉ |
| 209 | C₂H₅— | — | 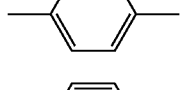 | F | —OCH₃ | H |
| 210 | C₂H₅— | — | 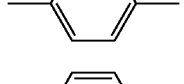 | F | —OC₂H₅ | H |
| 211 | C₂H₅— | — | 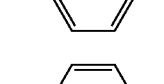 | F | —OC₃H₉ | H |
| 212 | C₂H₅— | — | 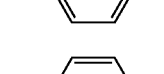 | F | —OC₄H₁₂ | H |
| 213 | C₃H₇— | — | 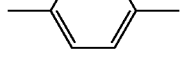 | F | —OCH₃ | H |

-continued
| No. | R¹¹ | A¹¹ | A¹² | Y | R²¹ | R²² |
|---|---|---|---|---|---|---|
| 214 | C₃H₇— | — |  | F | —OC₂H₅ | H |
| 215 | C₃H₇— | — | 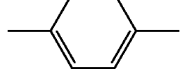 | F | —OC₃H₇ | H |
| 216 | C₃H₇— | — | 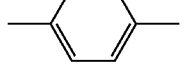 | F | —OC₄H₉ | H |
| 217 | C₄H₉— | — | 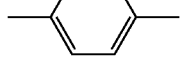 | F | —OCH₃ | H |
| 218 | C₄H₉— | — | 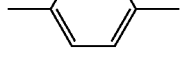 | F | —OC₂H₅ | H |
| 219 | C₄H₉— | — | 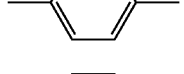 | F | —OC₃H₇ | H |
| 220 | C₄H₉— | — | 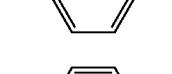 | F | —OC₄H₉ | H |
| 221 | C₅H₁₂— | — | 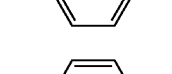 | F | —OCH₃ | H |
| 222 | C₅H₁₂— | — | 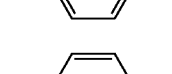 | F | —OC₂H₅ | H |
| 223 | C₅H₁₂— | — | 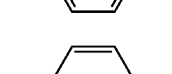 | F | —OC₃H₇ | H |
| 224 | C₅H₁₂— | — |  | F | —OC₄H₉ | H |
| 225 | C₂H₅— | — | 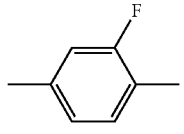 | F | —OCH₃ | H |
| 226 | C₂H₅— | — | 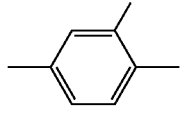 | F | —OC₂H₅ | H |
| 227 | C₂H₅— | — | 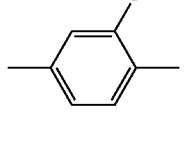 | F | —OC₃H₉ | H |

-continued
| No. | R¹¹ | A¹¹ | A¹² | Y | R²¹ | R²² |
|---|---|---|---|---|---|---|
| 228 | C₂H₅— | — | 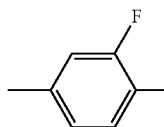 | F | —OC₄H₁₂ | H |
| 229 | C₃H₇— | — | 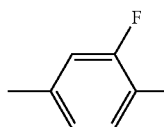 | F | —OCH₃ | H |
| 230 | C₃H₇— | — | 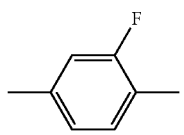 | F | —OC₂H₅ | H |
| 231 | C₃H₇— | — | 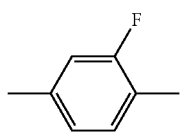 | F | —OC₃H₇ | H |
| 232 | C₃H₇— | — | 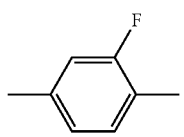 | F | —OC₄H₉ | H |
| 233 | C₄H₉— | — | 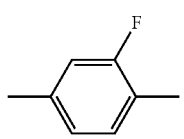 | F | —OCH₃ | H |
| 234 | C₄H₉— | — | 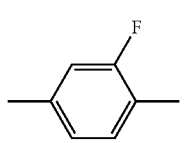 | F | —OC₂H₅ | H |
| 235 | C₄H₉— | — | 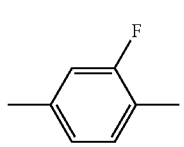 | F | —OC₃H₇ | H |
| 236 | C₄H₉— | — | 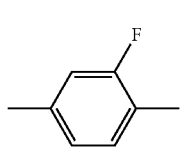 | F | —OC₄H₉ | H |
| 237 | C₅H₁₂— | — | 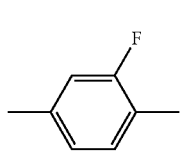 | F | —OCH₃ | H |
| 238 | C₅H₁₂— | — | 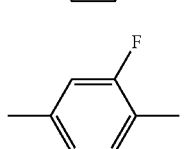 | F | —OC₂H₅ | H |

-continued
| No. | R¹¹ | A¹¹ | A¹² | Y | R²¹ | R²² |
|-----|-----|-----|-----|---|-----|-----|
| 239 | $C_5H_{12}$— | — | 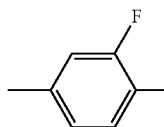 | F | —$OC_3H_7$ | H |
| 240 | $C_5H_{12}$— | — | 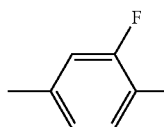 | F | —$OC_4H_9$ | H |
| 241 | $C_2H_5$— | — | 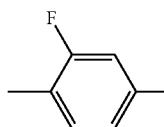 | F | —$OCH_3$ | H |
| 242 | $C_2H_5$— | — | 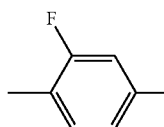 | F | —$OC_2H_5$ | H |
| 243 | $C_2H_5$— | — | 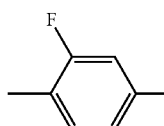 | F | —$OC_3H_9$ | H |
| 244 | $C_2H_5$— | — | 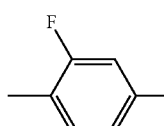 | F | —$OC_4H_{12}$ | H |
| 245 | $C_3H_7$— | — | 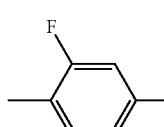 | F | —$OCH_3$ | H |
| 246 | $C_3H_7$— | — | 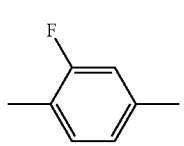 | F | —$OC_2H_5$ | H |
| 247 | $C_3H_7$— | — | 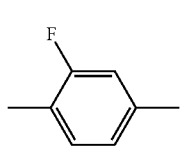 | F | —$OC_3H_7$ | H |
| 248 | $C_3H_7$— | — | 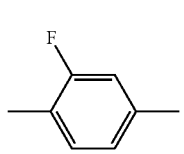 | F | —$OC_4H_9$ | H |
| 249 | $C_4H_9$— | — | 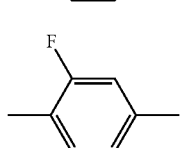 | F | —$OCH_3$ | H |

-continued
| No. | R¹¹ | A¹¹ | A¹² | Y | R²¹ | R²² |
|---|---|---|---|---|---|---|
| 250 | C₄H₉— | — | 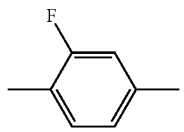 | F | —OC₂H₅ | H |
| 251 | C₄H₉— | — | 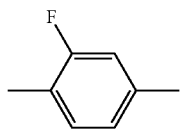 | F | —OC₃H₇ | H |
| 252 | C₄H₉— | — | 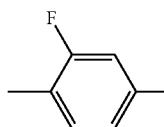 | F | —OC₄H₉ | H |
| 253 | C₅H₁₂— | — | 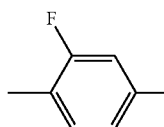 | F | —OCH₃ | H |
| 254 | C₅H₁₂— | — | 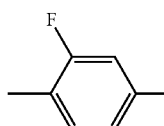 | F | —OC₂H₅ | H |
| 255 | C₅H₁₂— | — | 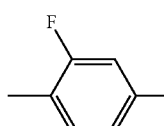 | F | —OC₃H₇ | H |
| 256 | C₅H₁₂— | — | 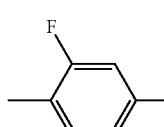 | F | —OC₄H₉ | H |
| 257 | C₂H₅— | — | 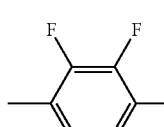 | F | —OCH₃ | H |
| 258 | C₂H₅— | — | 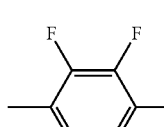 | F | —OC₂H₅ | H |
| 259 | C₂H₅— | — | 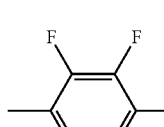 | F | —OC₃H₉ | H |
| 260 | C₂H₅— | — | 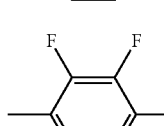 | F | —OC₄H₁₂ | H |

-continued
| No. | R11 | A11 | A12 | Y | R21 | R22 |
|---|---|---|---|---|---|---|
| 261 | C3H7— | — | 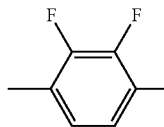 | F | —OCH3 | H |
| 262 | C3H7— | — | 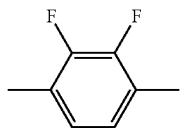 | F | —OC2H5 | H |
| 263 | C3H7— | — | 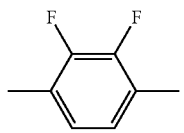 | F | —OC3H7 | H |
| 264 | C3H7— | — | 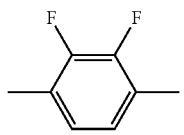 | F | —OC4H9 | H |
| 265 | C4H9— | — |  | F | —OCH3 | H |
| 266 | C4H9— | — | 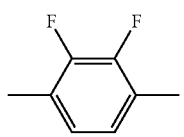 | F | —OC2H5 | H |
| 267 | C4H9— | — | 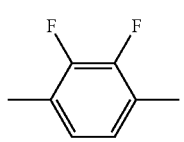 | F | —OC3H7 | H |
| 268 | C4H9— | — | 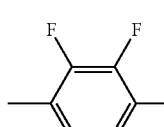 | F | —OC4H9 | H |
| 269 | C5H12— | — | 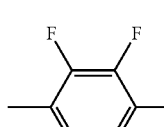 | F | —OCH3 | H |
| 270 | C5H12— | — | 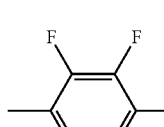 | F | —OC2H5 | H |
| 271 | C5H12— | — | 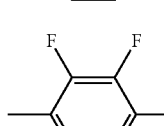 | F | —OC3H7 | H |

-continued
| No. | R¹¹ | A¹¹ | A¹² | Y | R²¹ | R²² |
|---|---|---|---|---|---|---|
| 272 | C₅H₁₂— | — | 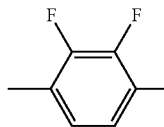 | F | —OC₄H₉ | H |
| 273 | C₂H₅— | — | 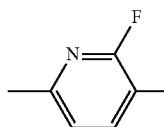 | F | —OCH₃ | H |
| 274 | C₂H₅— | — | 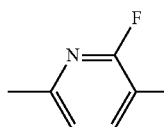 | F | —OC₂H₅ | H |
| 275 | C₂H₅— | — | 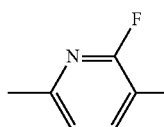 | F | —OC₃H₉ | H |
| 276 | C₂H₅— | — | 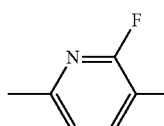 | F | —OC₄H₁₂ | H |
| 277 | C₃H₇— | — | 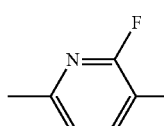 | F | —OCH₃ | H |
| 278 | C₃H₇— | — | 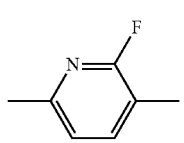 | F | —OC₂H₅ | H |
| 279 | C₃H₇— | — | 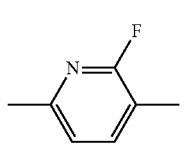 | F | —OC₃H₇ | H |
| 280 | C₃H₇— | — | 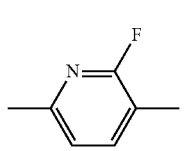 | F | —OC₄H₉ | H |
| 281 | C₄H₉— | — | 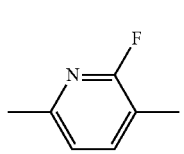 | F | —OCH₃ | H |
| 282 | C₄H₉— | — | 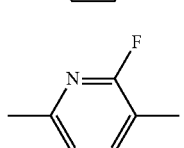 | F | —OC₂H₅ | H |

-continued
| No. | R¹¹ | A¹¹ | A¹² | Y | R²¹ | R²² |
|---|---|---|---|---|---|---|
| 283 | C₄H₉— | — | 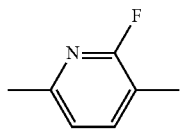 | F | —OC₃H₇ | H |
| 284 | C₄H₉— | — | 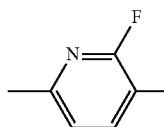 | F | —OC₄H₉ | H |
| 285 | C₅H₁₂— | — | 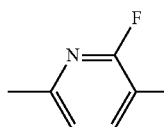 | F | —OCH₃ | H |
| 286 | C₅H₁₂— | — | 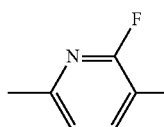 | F | —OC₂H₅ | H |
| 287 | C₅H₁₂— | — | 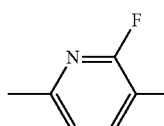 | F | —OC₃H₇ | H |
| 288 | C₅H₁₂— | — | 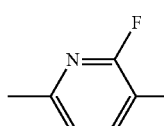 | F | —OC₄H₉ | H |
| 289 | C₂H₅— | — | 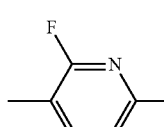 | F | —OCH₃ | H |
| 290 | C₂H₅— | — | 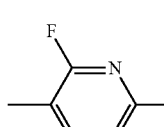 | F | —OC₂H₅ | H |
| 291 | C₂H₅— | — |  | F | —OC₃H₉ | H |
| 292 | C₂H₅— | — | 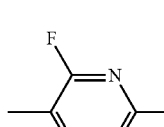 | F | —OC₄H₁₂ | H |
| 293 | C₃H₇— | — | 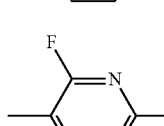 | F | —OCH₃ | H |

-continued
| No. | $R^{11}$ | $A^{11}$ | $A^{12}$ | Y | $R^{21}$ | $R^{22}$ |
|---|---|---|---|---|---|---|
| 294 | $C_3H_7$— | — |  | F | —$OC_2H_5$ | H |
| 295 | $C_3H_7$— | — | 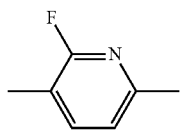 | F | —$OC_3H_7$ | H |
| 296 | $C_3H_7$— | — | 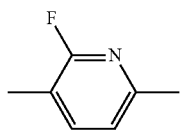 | F | —$OC_4H_9$ | H |
| 297 | $C_4H_9$— | — | 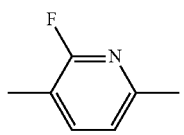 | F | —$OCH_3$ | H |
| 298 | $C_4H_9$— | — | 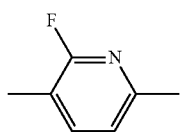 | F | —$OC_2H_5$ | H |
| 299 | $C_4H_9$— | — | 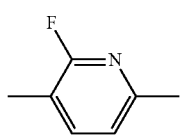 | F | —$OC_3H_7$ | H |
| 300 | $C_4H_9$— | — | 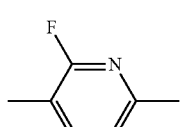 | F | —$OC_4H_9$ | H |
| 301 | $C_5H_{12}$— | — | 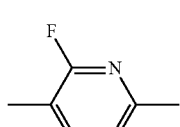 | F | —$OCH_3$ | H |
| 302 | $C_5H_{12}$— | — | 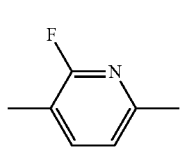 | F | —$OC_2H_5$ | H |
| 303 | $C_5H_{12}$— | — | 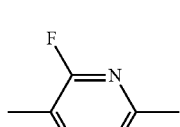 | F | —$OC_3H_7$ | H |
| 304 | $C_5H_{12}$— | — | 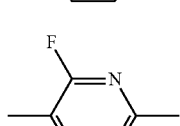 | F | —$OC_4H_9$ | H |

-continued
| No. | R[11] | A[11] | A[12] | Y | R[21] | R[22] |
|---|---|---|---|---|---|---|
| 305 | C$_2$H$_5$— | — | 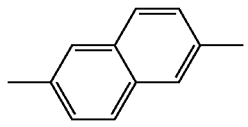 | F | —OCH$_3$ | H |
| 306 | C$_2$H$_5$— | — | 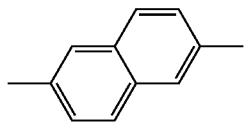 | F | —OC$_2$H$_5$ | H |
| 307 | C$_2$H$_5$— | — | 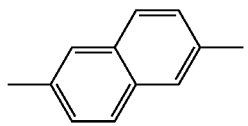 | F | —OC$_3$H$_9$ | H |
| 308 | C$_2$H$_5$— | — | 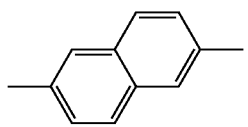 | F | —OC$_4$H$_{12}$ | H |
| 309 | C$_3$H$_7$— | — | 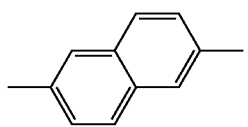 | F | —OCH$_3$ | H |
| 310 | C$_3$H$_7$— | — | 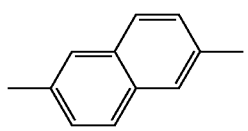 | F | —OC$_2$H$_5$ | H |
| 311 | C$_3$H$_7$— | — | 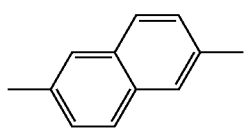 | F | —OC$_3$H$_7$ | H |
| 312 | C$_3$H$_7$— | — | 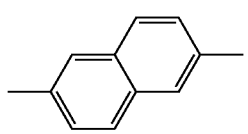 | F | —OC$_4$H$_9$ | H |
| 313 | C$_4$H$_9$— | — | 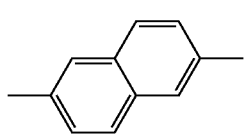 | F | —OCH$_3$ | H |
| 314 | C$_4$H$_9$— | — | 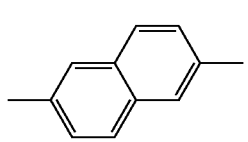 | F | —OC$_2$H$_5$ | H |
| 315 | C$_4$H$_9$— | — | 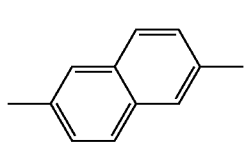 | F | —OC$_3$H$_7$ | H |

-continued

| No. | R¹¹ | A¹¹ | A¹² | Y | R²¹ | R²² |
|---|---|---|---|---|---|---|
| 316 | C₄H₉— | — | naphthalene-2,6-diyl | F | —OC₄H₉ | H |
| 317 | C₅H₁₂— | — | naphthalene-2,6-diyl | F | —OCH₃ | H |
| 318 | C₅H₁₂— | — | naphthalene-2,6-diyl | F | —OC₂H₅ | H |
| 319 | C₅H₁₂— | — | naphthalene-2,6-diyl | F | —OC₃H₇ | H |
| 320 | C₅H₁₂— | — | naphthalene-2,6-diyl | F | —OC₄H₉ | H |
| 321 | C₂H₅— | cyclohexane-1,4-diyl | phenylene | F | —OCH₃ | H |
| 322 | C₂H₅— | cyclohexane-1,4-diyl | phenylene | F | —OC₂H₅ | H |
| 323 | C₂H₅— | cyclohexane-1,4-diyl | phenylene | F | —OC₃H₉ | H |
| 324 | C₂H₅— | cyclohexane-1,4-diyl | phenylene | F | —OC₄H₁₂ | H |
| 325 | C₃H₇— | cyclohexane-1,4-diyl | phenylene | F | —OCH₃ | H |
| 326 | C₃H₇— | cyclohexane-1,4-diyl | phenylene | F | —OC₂H₅ | H |
| 327 | C₃H₇— | cyclohexane-1,4-diyl | phenylene | F | —OC₃H₇ | H |
| 328 | C₃H₇— | cyclohexane-1,4-diyl | phenylene | F | —OC₄H₉ | H |
| 329 | C₄H₉— | cyclohexane-1,4-diyl | phenylene | F | —OCH₃ | H |

-continued

| No. | R¹¹ | A¹¹ | A¹² | Y | R²¹ | R²² |
|---|---|---|---|---|---|---|
| 330 | C₄H₉— | cyclohexyl | phenyl | F | —OC₂H₅ | H |
| 331 | C₄H₉— | cyclohexyl | phenyl | F | —OC₃H₇ | H |
| 332 | C₄H₉— | cyclohexyl | phenyl | F | —OC₄H₉ | H |
| 333 | C₅H₁₂— | cyclohexyl | phenyl | F | —OCH₃ | H |
| 334 | C₅H₁₂— | cyclohexyl | phenyl | F | —OC₂H₅ | H |
| 335 | C₅H₁₂— | cyclohexyl | phenyl | F | —OC₃H₇ | H |
| 336 | C₅H₁₂— | cyclohexyl | phenyl | F | —OC₄H₉ | H |
| 337 | C₂H₅— | cyclohexyl | 2-fluorophenyl | F | —OCH₃ | H |
| 338 | C₂H₅— | cyclohexyl | 2-fluorophenyl | F | —OC₂H₅ | H |
| 339 | C₂H₅— | cyclohexyl | 2-fluorophenyl | F | —OC₃H₉ | H |
| 340 | C₂H₅— | cyclohexyl | 2-fluorophenyl | F | —OC₄H₁₂ | H |
| 341 | C₃H₇— | cyclohexyl | 2-fluorophenyl | F | —OCH₃ | H |
| 342 | C₃H₇— | cyclohexyl | 2-fluorophenyl | F | —OC₂H₅ | H |

-continued

| No. | R¹¹ | A¹¹ | A¹² | Y | R²¹ | R²² |
|---|---|---|---|---|---|---|
| 343 | C₃H₇— | cyclohexyl | 2-F phenyl | F | —OC₃H₇ | H |
| 344 | C₃H₇— | cyclohexyl | 2-F phenyl | F | —OC₄H₉ | H |
| 345 | C₄H₉— | cyclohexyl | 2-F phenyl | F | —OCH₃ | H |
| 346 | C₄H₉— | cyclohexyl | 2-F phenyl | F | —OC₂H₅ | H |
| 347 | C₄H₉— | cyclohexyl | 2-F phenyl | F | —OC₃H₇ | H |
| 348 | C₄H₉— | cyclohexyl | 2-F phenyl | F | —OC₄H₉ | H |
| 349 | C₅H₁₂— | cyclohexyl | 2-F phenyl | F | —OCH₃ | H |
| 350 | C₅H₁₂— | cyclohexyl | 2-F phenyl | F | —OC₂H₅ | H |
| 351 | C₅H₁₂— | cyclohexyl | 2-F phenyl | F | —OC₃H₇ | H |
| 352 | C₅H₁₂— | cyclohexyl | 2-F phenyl | F | —OC₄H₉ | H |
| 353 | C₂H₅— | cyclohexyl | 3-F phenyl | F | —OCH₃ | H |

-continued

| No. | R¹¹ | A¹¹ | A¹² | Y | R²¹ | R²² |
|---|---|---|---|---|---|---|
| 354 | C$_2$H$_5$— | cyclohexyl | 3-F phenyl | F | —OC$_2$H$_5$ | H |
| 355 | C$_2$H$_5$— | cyclohexyl | 3-F phenyl | F | —OC$_3$H$_9$ | H |
| 356 | C$_2$H$_5$— | cyclohexyl | 3-F phenyl | F | —OC$_4$H$_{12}$ | H |
| 357 | C$_3$H$_7$— | cyclohexyl | 3-F phenyl | F | —OCH$_3$ | H |
| 358 | C$_3$H$_7$— | cyclohexyl | 3-F phenyl | F | —OC$_2$H$_5$ | H |
| 359 | C$_3$H$_7$— | cyclohexyl | 3-F phenyl | F | —OC$_3$H$_7$ | H |
| 360 | C$_3$H$_7$— | cyclohexyl | 3-F phenyl | F | —OC$_4$H$_9$ | H |
| 361 | C$_4$H$_9$— | cyclohexyl | 3-F phenyl | F | —OCH$_3$ | H |
| 362 | C$_4$H$_9$— | cyclohexyl | 3-F phenyl | F | —OC$_2$H$_5$ | H |
| 363 | C$_4$H$_9$— | cyclohexyl | 3-F phenyl | F | —OC$_3$H$_7$ | H |
| 364 | C$_4$H$_9$— | cyclohexyl | 3-F phenyl | F | —OC$_4$H$_9$ | H |

-continued

| No. | R¹¹ | A¹¹ | A¹² | Y | R²¹ | R²² |
|---|---|---|---|---|---|---|
| 365 | C₅H₁₂— | cyclohexyl | 2-F phenyl | F | —OCH₃ | H |
| 366 | C₅H₁₂— | cyclohexyl | 2-F phenyl | F | —OC₂H₅ | H |
| 367 | C₅H₁₂— | cyclohexyl | 2-F phenyl | F | —OC₃H₇ | H |
| 368 | C₅H₁₂— | cyclohexyl | 2-F phenyl | F | —OC₄H₉ | H |
| 369 | C₂H₅— | cyclohexyl | 2,3-diF phenyl | F | —OCH₃ | H |
| 370 | C₂H₅— | cyclohexyl | 2,3-diF phenyl | F | —OC₂H₅ | H |
| 371 | C₂H₅— | cyclohexyl | 2,3-diF phenyl | F | —OC₃H₉ | H |
| 372 | C₂H₅— | cyclohexyl | 2,3-diF phenyl | F | —OC₄H₁₂ | H |
| 373 | C₃H₇— | cyclohexyl | 2,3-diF phenyl | F | —OCH₃ | H |
| 374 | C₃H₇— | cyclohexyl | 2,3-diF phenyl | F | —OC₂H₅ | H |
| 375 | C₃H₇— | cyclohexyl | 2,3-diF phenyl | F | —OC₃H₇ | H |

-continued

| No. | R¹¹ | A¹¹ | A¹² | Y | R²¹ | R²² |
|---|---|---|---|---|---|---|
| 376 | C₃H₇— | cyclohexyl | 2,3-difluorophenyl | F | —OC₄H₉ | H |
| 377 | C₄H₉— | cyclohexyl | 2,3-difluorophenyl | F | —OCH₃ | H |
| 378 | C₄H₉— | cyclohexyl | 2,3-difluorophenyl | F | —OC₂H₅ | H |
| 379 | C₄H₉— | cyclohexyl | 2,3-difluorophenyl | F | —OC₃H₇ | H |
| 380 | C₄H₉— | cyclohexyl | 2,3-difluorophenyl | F | —OC₄H₉ | H |
| 381 | C₅H₁₂— | cyclohexyl | 2,3-difluorophenyl | F | —OCH₃ | H |
| 382 | C₅H₁₂— | cyclohexyl | 2,3-difluorophenyl | F | —OC₂H₅ | H |
| 383 | C₅H₁₂— | cyclohexyl | 2,3-difluorophenyl | F | —OC₃H₇ | H |
| 384 | C₅H₁₂— | cyclohexyl | 2,3-difluorophenyl | F | —OC₄H₉ | H |
| 385 | C₂H₅— | cyclohexyl | 2-fluoropyridyl | F | —OCH₃ | H |
| 386 | C₂H₅— | cyclohexyl | 2-fluoropyridyl | F | —OC₂H₅ | H |

-continued

| No. | R¹¹ | A¹¹ | A¹² | Y | R²¹ | R²² |
|---|---|---|---|---|---|---|
| 387 | C₂H₅— | cyclohexyl | 2-F,6-pyridyl (F) | F | —OC₃H₉ | H |
| 388 | C₂H₅— | cyclohexyl | 2-F,6-pyridyl (F) | F | —OC₄H₁₂ | H |
| 389 | C₃H₇— | cyclohexyl | 2-F,6-pyridyl (F) | F | —OCH₃ | H |
| 390 | C₃H₇— | cyclohexyl | 2-F,6-pyridyl (F) | F | —OC₂H₅ | H |
| 391 | C₃H₇— | cyclohexyl | 2-F,6-pyridyl (F) | F | —OC₃H₇ | H |
| 392 | C₃H₇— | cyclohexyl | 2-F,6-pyridyl (F) | F | —OC₄H₉ | H |
| 393 | C₄H₉— | cyclohexyl | 2-F,6-pyridyl (F) | F | —OCH₃ | H |
| 394 | C₄H₉— | cyclohexyl | 2-F,6-pyridyl (F) | F | —OC₂H₅ | H |
| 395 | C₄H₉— | cyclohexyl | 2-F,6-pyridyl (F) | F | —OC₃H₇ | H |
| 396 | C₄H₉— | cyclohexyl | 2-F,6-pyridyl (F) | F | —OC₄H₉ | H |
| 397 | C₅H₁₂— | cyclohexyl | 2-F,6-pyridyl (F) | F | —OCH₃ | H |

-continued

| No. | R¹¹ | A¹¹ | A¹² | Y | R²¹ | R²² |
|---|---|---|---|---|---|---|
| 398 | C₅H₁₂— | cyclohexyl | 2-F,6-pyridyl (F at 3) | F | —OC₂H₅ | H |
| 399 | C₅H₁₂— | cyclohexyl | 2-F,6-pyridyl (F at 3) | F | —OC₃H₇ | H |
| 400 | C₅H₁₂— | cyclohexyl | 2-F,6-pyridyl (F at 3) | F | —OC₄H₉ | H |
| 401 | C₂H₅— | cyclohexyl | 2-F,6-pyridyl | F | —OCH₃ | H |
| 402 | C₂H₅— | cyclohexyl | 2-F,6-pyridyl | F | —OC₂H₅ | H |
| 403 | C₂H₅— | cyclohexyl | 2-F,6-pyridyl | F | —OC₃H₉ | H |
| 404 | C₂H₅— | cyclohexyl | 2-F,6-pyridyl | F | —OC₄H₁₂ | H |
| 405 | C₃H₇— | cyclohexyl | 2-F,6-pyridyl | F | —OCH₃ | H |
| 406 | C₃H₇— | cyclohexyl | 2-F,6-pyridyl | F | —OC₂H₅ | H |
| 407 | C₃H₇— | cyclohexyl | 2-F,6-pyridyl | F | —OC₃H₇ | H |
| 408 | C₃H₇— | cyclohexyl | 2-F,6-pyridyl | F | —OC₄H₉ | H |

-continued

| No. | R$^{11}$ | A$^{11}$ | A$^{12}$ | Y | R$^{21}$ | R$^{22}$ |
|---|---|---|---|---|---|---|
| 409 | C$_4$H$_9$— | cyclohexyl | 2-F-pyridine | F | —OCH$_3$ | H |
| 410 | C$_4$H$_9$— | cyclohexyl | 2-F-pyridine | F | —OC$_2$H$_5$ | H |
| 411 | C$_4$H$_9$— | cyclohexyl | 2-F-pyridine | F | —OC$_3$H$_7$ | H |
| 412 | C$_4$H$_9$— | cyclohexyl | 2-F-pyridine | F | —OC$_4$H$_9$ | H |
| 413 | C$_5$H$_{12}$— | cyclohexyl | 2-F-pyridine | F | —OCH$_3$ | H |
| 414 | C$_5$H$_{12}$— | cyclohexyl | 2-F-pyridine | F | —OC$_2$H$_5$ | H |
| 415 | C$_5$H$_{12}$— | cyclohexyl | 2-F-pyridine | F | —OC$_3$H$_7$ | H |
| 416 | C$_5$H$_{12}$— | cyclohexyl | 2-F-pyridine | F | —OC$_4$H$_9$ | H |
| 417 | C$_2$H$_5$— | phenyl | phenyl | F | —OCH$_3$ | H |
| 418 | C$_2$H$_5$— | phenyl | phenyl | F | —OC$_2$H$_5$ | H |
| 419 | C$_2$H$_5$— | phenyl | phenyl | F | —OC$_3$H$_9$ | H |
| 420 | C$_2$H$_5$— | phenyl | phenyl | F | —OC$_4$H$_{12}$ | H |

-continued
| No. | R¹¹ | A¹¹ | A¹² | Y | R²¹ | R²² |
|---|---|---|---|---|---|---|
| 421 | C₃H₇— | 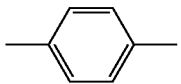 |  | F | —OCH₃ | H |
| 422 | C₃H₇— | 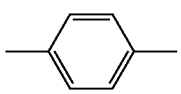 | 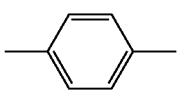 | F | —OC₂H₅ | H |
| 423 | C₃H₇— |  |  | F | —OC₃H₇ | H |
| 424 | C₃H₇— | 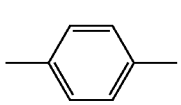 | 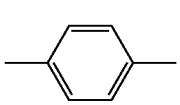 | F | —OC₄H₉ | H |
| 425 | C₄H₉— | 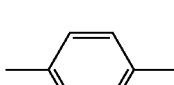 | 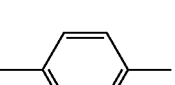 | F | —OCH₃ | H |
| 426 | C₄H₉— | 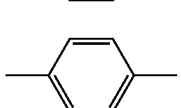 | 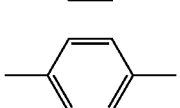 | F | —OC₂H₅ | H |
| 427 | C₄H₉— | 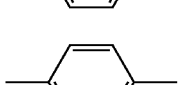 | 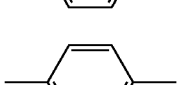 | F | —OC₃H₇ | H |
| 428 | C₄H₉— | 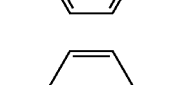 | 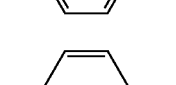 | F | —OC₄H₉ | H |
| 429 | C₅H₁₂— |  | 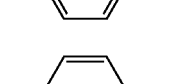 | F | —OCH₃ | H |
| 430 | C₅H₁₂— | 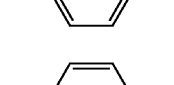 | 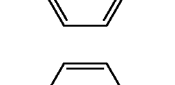 | F | —OC₂H₅ | H |
| 431 | C₅H₁₂— | 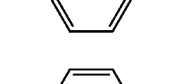 | 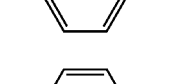 | F | —OC₃H₇ | H |
| 432 | C₅H₁₂— | 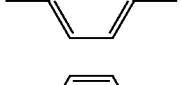 | 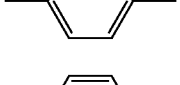 | F | —OC₄H₉ | H |
| 433 | C₂H₅— | 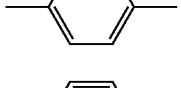 | 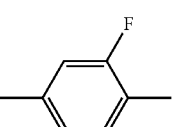 | F | —OCH₃ | H |
| 434 | C₂H₅— | 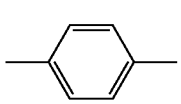 | 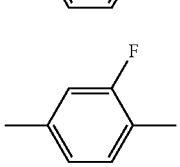 | F | —OC₂H₅ | H |

-continued

| No. | R¹¹ | A¹¹ | A¹² | Y | R²¹ | R²² |
|---|---|---|---|---|---|---|
| 435 | C₂H₅— | phenylene | 2-fluorophenylene | F | —OC₃H₉ | H |
| 436 | C₂H₅— | phenylene | 2-fluorophenylene | F | —OC₄H₁₂ | H |
| 437 | C₃H₇— | phenylene | 2-fluorophenylene | F | —OCH₃ | H |
| 438 | C₃H₇— | phenylene | 2-fluorophenylene | F | —OC₂H₅ | H |
| 439 | C₃H₇— | phenylene | 2-fluorophenylene | F | —OC₃H₇ | H |
| 440 | C₃H₇— | phenylene | 2-fluorophenylene | F | —OC₄H₉ | H |
| 441 | C₄H₉— | phenylene | 2-fluorophenylene | F | —OCH₃ | H |
| 442 | C₄H₉— | phenylene | 2-fluorophenylene | F | —OC₂H₅ | H |
| 443 | C₄H₉— | phenylene | 2-fluorophenylene | F | —OC₃H₇ | H |
| 444 | C₄H₉— | phenylene | 2-fluorophenylene | F | —OC₄H₉ | H |
| 445 | C₅H₁₂— | phenylene | 2-fluorophenylene | F | —OCH₃ | H |

-continued

| No. | R¹¹ | A¹¹ | A¹² | Y | R²¹ | R²² |
|---|---|---|---|---|---|---|
| 446 | C₅H₁₂— | phenyl | 3-F phenyl | F | —OC₂H₅ | H |
| 447 | C₅H₁₂— | phenyl | 3-F phenyl | F | —OC₃H₇ | H |
| 448 | C₅H₁₂— | phenyl | 3-F phenyl | F | —OC₄H₉ | H |
| 449 | C₂H₅— | phenyl | 2-F phenyl | F | —OCH₃ | H |
| 450 | C₂H₅— | phenyl | 2-F phenyl | F | —OC₂H₅ | H |
| 451 | C₂H₅— | phenyl | 2-F phenyl | F | —OC₃H₉ | H |
| 452 | C₂H₅— | phenyl | 2-F phenyl | F | —OC₄H₁₂ | H |
| 453 | C₃H₇— | phenyl | 2-F phenyl | F | —OCH₃ | H |
| 454 | C₃H₇— | phenyl | 2-F phenyl | F | —OC₂H₅ | H |
| 455 | C₃H₇— | phenyl | 2-F phenyl | F | —OC₃H₇ | H |
| 456 | C₃H₇— | phenyl | 2-F phenyl | F | —OC₄H₉ | H |

-continued

| No. | R¹¹ | A¹¹ | A¹² | Y | R²¹ | R²² |
|---|---|---|---|---|---|---|
| 457 | C₄H₉— | phenyl | 2-F-phenyl | F | —OCH₃ | H |
| 458 | C₄H₉— | phenyl | 2-F-phenyl | F | —OC₂H₅ | H |
| 459 | C₄H₉— | phenyl | 2-F-phenyl | F | —OC₃H₇ | H |
| 460 | C₄H₉— | phenyl | 2-F-phenyl | F | —OC₄H₉ | H |
| 461 | C₅H₁₂— | phenyl | 2-F-phenyl | F | —OCH₃ | H |
| 462 | C₅H₁₂— | phenyl | 2-F-phenyl | F | —OC₂H₅ | H |
| 463 | C₅H₁₂— | phenyl | 2-F-phenyl | F | —OC₃H₇ | H |
| 464 | C₅H₁₂— | phenyl | 2-F-phenyl | F | —OC₄H₉ | H |
| 465 | C₂H₅— | phenyl | 2,3-diF-phenyl | F | —OCH₃ | H |
| 466 | C₂H₅— | phenyl | 2,3-diF-phenyl | F | —OC₂H₅ | H |
| 467 | C₂H₅— | phenyl | 2,3-diF-phenyl | F | —OC₃H₉ | H |

-continued

| No. | R¹¹ | A¹¹ | A¹² | Y | R²¹ | R²² |
|---|---|---|---|---|---|---|
| 468 | C₂H₅— | phenylene | 2,3-difluorophenylene | F | —OC₄H₁₂ | H |
| 469 | C₃H₇— | phenylene | 2,3-difluorophenylene | F | —OCH₃ | H |
| 470 | C₃H₇— | phenylene | 2,3-difluorophenylene | F | —OC₂H₅ | H |
| 471 | C₃H₇— | phenylene | 2,3-difluorophenylene | F | —OC₃H₇ | H |
| 472 | C₃H₇— | phenylene | 2,3-difluorophenylene | F | —OC₄H₉ | H |
| 473 | C₄H₉— | phenylene | 2,3-difluorophenylene | F | —OCH₃ | H |
| 474 | C₄H₉— | phenylene | 2,3-difluorophenylene | F | —OC₂H₅ | H |
| 475 | C₄H₉— | phenylene | 2,3-difluorophenylene | F | —OC₃H₇ | H |
| 476 | C₄H₉— | phenylene | 2,3-difluorophenylene | F | —OC₄H₉ | H |
| 477 | C₅H₁₂— | phenylene | 2,3-difluorophenylene | F | —OCH₃ | H |
| 478 | C₅H₁₂— | phenylene | 2,3-difluorophenylene | F | —OC₂H₅ | H |

-continued

| No. | R¹¹ | A¹¹ | A¹² | Y | R²¹ | R²² |
|---|---|---|---|---|---|---|
| 479 | C₅H₁₂— | phenylene | 2,3-difluorophenylene | F | —OC₃H₇ | H |
| 480 | C₅H₁₂— | phenylene | 2,3-difluorophenylene | F | —OC₄H₉ | H |
| 481 | C₂H₅— | phenylene | 2-fluoropyridine | F | —OCH₃ | H |
| 482 | C₂H₅— | phenylene | 2-fluoropyridine | F | —OC₂H₅ | H |
| 483 | C₂H₅— | phenylene | 2-fluoropyridine | F | —OC₃H₉ | H |
| 484 | C₂H₅— | phenylene | 2-fluoropyridine | F | —OC₄H₁₂ | H |
| 485 | C₃H₇— | phenylene | 2-fluoropyridine | F | —OCH₃ | H |
| 486 | C₃H₇— | phenylene | 2-fluoropyridine | F | —OC₂H₅ | H |
| 487 | C₃H₇— | phenylene | 2-fluoropyridine | F | —OC₃H₇ | H |
| 488 | C₃H₇— | phenylene | 2-fluoropyridine | F | —OC₄H₉ | H |
| 489 | C₄H₉— | phenylene | 2-fluoropyridine | F | —OCH₃ | H |

-continued

| No. | R¹¹ | A¹¹ | A¹² | Y | R²¹ | R²² |
|---|---|---|---|---|---|---|
| 490 | C₄H₉— | -⟨phenyl⟩- | 2-F,pyridine | F | —OC₂H₅ | H |
| 491 | C₄H₉— | -⟨phenyl⟩- | 2-F,pyridine | F | —OC₃H₇ | H |
| 492 | C₄H₉— | -⟨phenyl⟩- | 2-F,pyridine | F | —OC₄H₉ | H |
| 493 | C₅H₁₂— | -⟨phenyl⟩- | 2-F,pyridine | F | —OCH₃ | H |
| 494 | C₅H₁₂— | -⟨phenyl⟩- | 2-F,pyridine | F | —OC₂H₅ | H |
| 495 | C₅H₁₂— | -⟨phenyl⟩- | 2-F,pyridine | F | —OC₃H₇ | H |
| 496 | C₅H₁₂— | -⟨phenyl⟩- | 2-F,pyridine | F | —OC₄H₉ | H |
| 497 | C₂H₅— | -⟨phenyl⟩- | 2-F,pyridine | F | —OCH₃ | H |
| 498 | C₂H₅— | -⟨phenyl⟩- | 2-F,pyridine | F | —OC₂H₅ | H |
| 499 | C₂H₅— | -⟨phenyl⟩- | 2-F,pyridine | F | —OC₃H₉ | H |
| 500 | C₂H₅— | -⟨phenyl⟩- | 2-F,pyridine | F | —OC₄H₁₂ | H |

-continued

| No. | R¹¹ | A¹¹ | A¹² | Y | R²¹ | R²² |
|---|---|---|---|---|---|---|
| 501 | C₃H₇— | phenylene | 2-F,3-pyridine | F | —OCH₃ | H |
| 502 | C₃H₇— | phenylene | 2-F,3-pyridine | F | —OC₂H₅ | H |
| 503 | C₃H₇— | phenylene | 2-F,3-pyridine | F | —OC₃H₇ | H |
| 504 | C₃H₇— | phenylene | 2-F,3-pyridine | F | —OC₄H₉ | H |
| 505 | C₄H₉— | phenylene | 2-F,3-pyridine | F | —OCH₃ | H |
| 506 | C₄H₉— | phenylene | 2-F,3-pyridine | F | —OC₂H₅ | H |
| 507 | C₄H₉— | phenylene | 2-F,3-pyridine | F | —OC₃H₇ | H |
| 508 | C₄H₉— | phenylene | 2-F,3-pyridine | F | —OC₄H₉ | H |
| 509 | C₅H₁₂— | phenylene | 2-F,3-pyridine | F | —OCH₃ | H |
| 510 | C₅H₁₂— | phenylene | 2-F,3-pyridine | F | —OC₂H₅ | H |
| 511 | C₅H₁₂— | phenylene | 2-F,3-pyridine | F | —OC₃H₇ | H |

-continued

| No. | R¹¹ | A¹¹ | A¹² | Y | R²¹ | R²² |
|---|---|---|---|---|---|---|
| 512 | C₅H₁₂— | phenyl | 2-fluoropyridyl | F | —OC₄H₉ | H |
| 513 | C₂H₅— | cyclohexyl | phenyl | F | —OCH₃ | H |
| 514 | C₂H₅— | cyclohexyl | phenyl | F | —OC₂H₅ | H |
| 515 | C₂H₅— | cyclohexyl | phenyl | F | —OC₃H₉ | H |
| 516 | C₂H₅— | cyclohexyl | phenyl | F | —OC₄H₁₂ | H |
| 517 | C₃H₇— | cyclohexyl | phenyl | F | —OCH₃ | H |
| 518 | C₃H₇— | cyclohexyl | phenyl | F | —OC₂H₅ | H |
| 519 | C₃H₇— | cyclohexyl | phenyl | F | —OC₃H₇ | H |
| 520 | C₃H₇— | cyclohexyl | phenyl | F | —OC₄H₉ | H |
| 521 | C₄H₉— | cyclohexyl | phenyl | F | —OCH₃ | H |
| 522 | C₄H₉— | cyclohexyl | fluoropyridyl | F | —OC₂H₅ | H |
| 523 | C₄H₉— | cyclohexyl | phenyl | F | —OC₃H₇ | H |
| 524 | C₄H₉— | cyclohexyl | phenyl | F | —OC₄H₉ | H |
| 525 | C₅H₁₂— | cyclohexyl | phenyl | F | —OCH₃ | H |
| 526 | C₅H₁₂— | cyclohexyl | phenyl | F | —OC₂H₅ | H |

-continued

| No. | R¹¹ | A¹¹ | A¹² | Y | R²¹ | R²² |
|---|---|---|---|---|---|---|
| 527 | C₅H₁₂— | cyclohexyl | phenyl | F | —OC₃H₇ | H |
| 528 | C₅H₁₂— | cyclohexyl | phenyl | F | —OC₄H₉ | H |
| 529 | C₂H₅— | cyclohexyl | 2-F-phenyl | F | —OCH₃ | H |
| 530 | C₂H₅— | cyclohexyl | 2-F-phenyl | F | —OC₂H₅ | H |
| 531 | C₂H₅— | cyclohexyl | 2-F-phenyl | F | —OC₃H₉ | H |
| 532 | C₂H₅— | cyclohexyl | 2-F-phenyl | F | —OC₄H₁₂ | H |
| 533 | C₃H₇— | cyclohexyl | 2-F-phenyl | F | —OCH₃ | H |
| 534 | C₃H₇— | cyclohexyl | 2-F-phenyl | F | —OC₂H₅ | H |
| 535 | C₃H₇— | cyclohexyl | 2-F-phenyl | F | —OC₃H₇ | H |
| 536 | C₃H₇— | cyclohexyl | 2-F-phenyl | F | —OC₄H₉ | H |
| 537 | C₄H₉— | cyclohexyl | 2-F-phenyl | F | —OCH₃ | H |

-continued

| No. | R¹¹ | A¹¹ | A¹² | Y | R²¹ | R²² |
|---|---|---|---|---|---|---|
| 538 | C₄H₉— | cyclohexyl | 3-F phenyl | F | —OC₂H₅ | H |
| 539 | C₄H₉— | cyclohexyl | 3-F phenyl | F | —OC₃H₇ | H |
| 540 | C₄H₉— | cyclohexyl | 3-F phenyl | F | —OC₄H₉ | H |
| 541 | C₅H₁₂— | cyclohexyl | 3-F phenyl | F | —OCH₃ | H |
| 542 | C₅H₁₂— | cyclohexyl | 3-F phenyl | F | —OC₂H₅ | H |
| 543 | C₅H₁₂— | cyclohexyl | 3-F phenyl | F | —OC₃H₇ | H |
| 544 | C₅H₁₂— | cyclohexyl | 3-F phenyl | F | —OC₄H₉ | H |
| 545 | C₂H₅— | cyclohexyl | 2-F phenyl | F | —OCH₃ | H |
| 546 | C₂H₅— | cyclohexyl | 2-F phenyl | F | —OC₂H₅ | H |
| 547 | C₂H₅— | cyclohexyl | 2-F phenyl | F | —OC₃H₉ | H |
| 548 | C₂H₅— | cyclohexyl | 2-F phenyl | F | —OC₄H₁₂ | H |

-continued

| No. | R¹¹ | A¹¹ | A¹² | Y | R²¹ | R²² |
|---|---|---|---|---|---|---|
| 549 | C₃H₇— | cyclohexyl | 3-F phenyl | F | —OCH₃ | H |
| 550 | C₃H₇— | cyclohexyl | 3-F phenyl | F | —OC₂H₅ | H |
| 551 | C₃H₇— | cyclohexyl | 3-F phenyl | F | —OC₃H₇ | H |
| 552 | C₃H₇— | cyclohexyl | 3-F phenyl | F | —OC₄H₉ | H |
| 553 | C₄H₉— | cyclohexyl | 3-F phenyl | F | —OCH₃ | H |
| 554 | C₄H₉— | cyclohexyl | 3-F phenyl | F | —OC₂H₅ | H |
| 555 | C₄H₉— | cyclohexyl | 3-F phenyl | F | —OC₃H₇ | H |
| 556 | C₄H₉— | cyclohexyl | 3-F phenyl | F | —OC₄H₉ | H |
| 557 | C₅H₁₂— | cyclohexyl | 3-F phenyl | F | —OCH₃ | H |
| 558 | C₅H₁₂— | cyclohexyl | 3-F phenyl | F | —OC₂H₅ | H |
| 559 | C₅H₁₂— | cyclohexyl | 3-F phenyl | F | —OC₃H₇ | H |

-continued

| No. | R¹¹ | A¹¹ | A¹² | Y | R²¹ | R²² |
|---|---|---|---|---|---|---|
| 560 | C₅H₁₂— | cyclohexyl | 2-F phenyl | F | —OC₄H₉ | H |
| 561 | C₂H₅— | cyclohexyl | 2,3-diF phenyl | F | —OCH₃ | H |
| 562 | C₂H₅— | cyclohexyl | 2,3-diF phenyl | F | —OC₂H₅ | H |
| 563 | C₂H₅— | cyclohexyl | 2,3-diF phenyl | F | —OC₃H₉ | H |
| 564 | C₂H₅— | cyclohexyl | 2,3-diF phenyl | F | —OC₄H₁₂ | H |
| 565 | C₃H₇— | cyclohexyl | 2,3-diF phenyl | F | —OCH₃ | H |
| 566 | C₃H₇— | cyclohexyl | 2,3-diF phenyl | F | —OC₂H₅ | H |
| 567 | C₃H₇— | cyclohexyl | 2,3-diF phenyl | F | —OC₃H₇ | H |
| 568 | C₃H₇— | cyclohexyl | 2,3-diF phenyl | F | —OC₄H₉ | H |
| 569 | C₄H₉— | cyclohexyl | 2,3-diF phenyl | F | —OCH₃ | H |
| 570 | C₄H₉— | cyclohexyl | 2,3-diF phenyl | F | —OC₂H₅ | H |

-continued

| No. | R¹¹ | A¹¹ | A¹² | Y | R²¹ | R²² |
|---|---|---|---|---|---|---|
| 571 | C₄H₉— | cyclohexyl | 2,3-difluorobenzene | F | —OC₃H₇ | H |
| 572 | C₄H₉— | cyclohexyl | 2,3-difluorobenzene | F | —OC₄H₉ | H |
| 573 | C₅H₁₂— | cyclohexyl | 2,3-difluorobenzene | F | —OCH₃ | H |
| 574 | C₅H₁₂— | cyclohexyl | 2,3-difluorobenzene | F | —OC₂H₅ | H |
| 575 | C₅H₁₂— | cyclohexyl | 2,3-difluorobenzene | F | —OC₃H₇ | H |
| 576 | C₅H₁₂— | cyclohexyl | 2,3-difluorobenzene | F | —OC₄H₉ | H |
| 577 | C₂H₅— | cyclohexyl | 2-fluoropyridine | F | —OCH₃ | H |
| 578 | C₂H₅— | cyclohexyl | 2-fluoropyridine | F | —OC₂H₅ | H |
| 579 | C₂H₅— | cyclohexyl | 2-fluoropyridine | F | —OC₃H₉ | H |
| 580 | C₂H₅— | cyclohexyl | 2-fluoropyridine | F | —OC₄H₁₂ | H |
| 581 | C₃H₇— | cyclohexyl | 2-fluoropyridine | F | —OCH₃ | H |

-continued

| No. | R¹¹ | A¹¹ | A¹² | Y | R²¹ | R²² |
|---|---|---|---|---|---|---|
| 582 | C₃H₇— | cyclohexyl | 2-F,pyridyl | F | —OC₂H₅ | H |
| 583 | C₃H₇— | cyclohexyl | 2-F,pyridyl | F | —OC₃H₇ | H |
| 584 | C₃H₇— | cyclohexyl | 2-F,pyridyl | F | —OC₄H₉ | H |
| 585 | C₄H₉— | cyclohexyl | 2-F,pyridyl | F | —OCH₃ | H |
| 586 | C₄H₉— | cyclohexyl | 2-F,pyridyl | F | —OC₂H₅ | H |
| 587 | C₄H₉— | cyclohexyl | 2-F,pyridyl | F | —OC₃H₇ | H |
| 588 | C₄H₉— | cyclohexyl | 2-F,pyridyl | F | —OC₄H₉ | H |
| 589 | C₅H₁₂— | cyclohexyl | 2-F,pyridyl | F | —OCH₃ | H |
| 590 | C₅H₁₂— | cyclohexyl | 2-F,pyridyl | F | —OC₂H₅ | H |
| 591 | C₅H₁₂— | cyclohexyl | 2-F,pyridyl | F | —OC₃H₇ | H |
| 592 | C₅H₁₂— | cyclohexyl | 2-F,pyridyl | F | —OC₄H₉ | H |

-continued

| No. | R¹¹ | A¹¹ | A¹² | Y | R²¹ | R²² |
|---|---|---|---|---|---|---|
| 593 | C₂H₅— | cyclohexyl | 3-F pyridine | F | —OCH₃ | H |
| 594 | C₂H₅— | cyclohexyl | 3-F pyridine | F | —OC₂H₅ | H |
| 595 | C₂H₅— | cyclohexyl | 3-F pyridine | F | —OC₃H₉ | H |
| 596 | C₂H₅— | cyclohexyl | 3-F pyridine | F | —OC₄H₁₂ | H |
| 597 | C₃H₇— | cyclohexyl | 3-F pyridine | F | —OCH₃ | H |
| 598 | C₃H₇— | cyclohexyl | 3-F pyridine | F | —OC₂H₅ | H |
| 599 | C₃H₇— | cyclohexyl | 3-F pyridine | F | —OC₃H₇ | H |
| 600 | C₃H₇— | cyclohexyl | 3-F pyridine | F | —OC₄H₉ | H |
| 601 | C₄H₉— | cyclohexyl | 3-F pyridine | F | —OCH₃ | H |
| 602 | C₄H₉— | cyclohexyl | 3-F pyridine | F | —OC₂H₅ | H |
| 603 | C₄H₉— | cyclohexyl | 3-F pyridine | F | —OC₃H₇ | H |

| No. | R¹¹ | A¹¹ | A¹² | Y | R²¹ | R²² |
|---|---|---|---|---|---|---|
| 604 | $C_4H_9-$ | (cyclohexylene) | (2-F,3-methyl,6-methyl pyridine) | F | $-OC_4H_9$ | H |
| 605 | $C_5H_{12}-$ | (cyclohexylene) | (2-F,3-methyl,6-methyl pyridine) | F | $-OCH_3$ | H |
| 606 | $C_5H_{12}-$ | (cyclohexylene) | (2-F,3-methyl,6-methyl pyridine) | F | $-OC_2H_5$ | H |
| 607 | $C_5H_{12}-$ | (cyclohexylene) | (2-F,3-methyl,6-methyl pyridine) | F | $-OC_3H_7$ | H |
| 608 | $C_5H_{12}-$ | (cyclohexylene) | (2-F,3-methyl,6-methyl pyridine) | F | $-OC_4H_9$ | H |

The compounds are distinguished by a high negative dielectric anisotropy and high clearing temperatures which makes them very suitable for applications in liquid crystalline media for VA, IPS and FFS displays.

The invention claimed is:

1. A compound of formula I

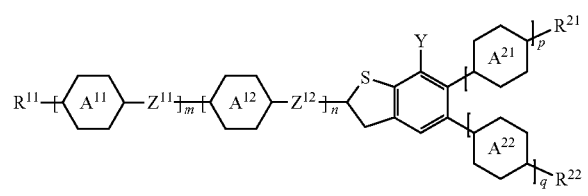

I in which $R^{11}$, $R^{21}$ and $R^{22}$ each, identically or differently, denote H, F, Cl, Br, I, CN, SCN, OH, $SF_5$, straight chain or branched alkyl with up to 15 C atoms which may be unsubstituted, mono- or polysubstituted by F, Cl, Br, I or CN, one or more non-adjacent $CH_2$ groups optionally being replaced, in each case independently of one another, by

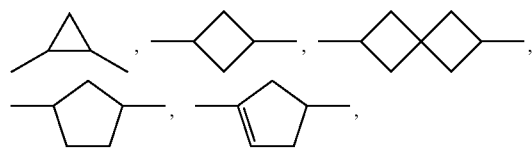

—O—, —S—, —NH—, —NR⁰—, —C(O)—, —C(O)O—, —OC(O)—, —OC(O)O—, —S—C(O)—, —CO—S—, —CH=CH— or —C≡C— in such a manner that O and/or S atoms are not linked directly to one another, $A^{11}$, $A^{12}$ $A^{21}$ and $A^{22}$ each, independently of one another, denote:
a) trans-1,4-cyclohexylene, 1,4-cyclohexenylene, or decaline-2,6-diyl, in which one or more non-adjacent $CH_2$ groups are optionally replaced by —O— and/or —S— and in which one or more H atoms are optionally replaced by F,
b) 1,4-phenylene or 2,6-naphthylene, in which one or two CH groups are optionally replaced by N and in which, in addition, one or more H atoms are optionally replaced by L,
c) 1,3-dioxane-2,5-diyl, tetrahydrofuran-2,5-diyl, cyclobutane-1,3-diyl, thiophene-2,5-diyl, selenophene-2,5-diyl, or 1,2,3,4-tetrahydronanaphthaline-2,6-diyl, each of which is optionally mono- or polysubstituted by L,
d) bicyclo[1.1.1]pentane-1,3-diyl, bicyclo[2.2.2]octane-1,4-diyl, or spiro[3.3]heptane-2,6-diyl, in which one or more H atoms is optionally replaced by F L each, identically or differently, denote halogen, cyano, alkyl, alkoxy, alkylcarbonyl or alkoxycarbonyl group with 1 to 7 C atoms, wherein one or more H atoms is optionally substituted by F or Cl, $Z^{11}$ and $Z^{12}$ independently of one another, denote a single bond, —$CF_2O$—, —$OCF_2$—, —$CH_2CH_2$—, —CF$_2$CF$_2$—, —C(O)O—, —OC(O)—, —CH$_2$O—, —OCH$_2$—, —CF=CH—, —CH=CF—, —CF=CF—, —CH=CH— or —C≡C—, Y denotes H, F, Cl, CF$_3$, or OCF$_3$, and m and n are, independently of one another, 0, 1 or 2, with the proviso that at least one of m and n denotes 0.

2. The compound of formula I according to claim 1, wherein the compound is a compound of the sub-formula Ia

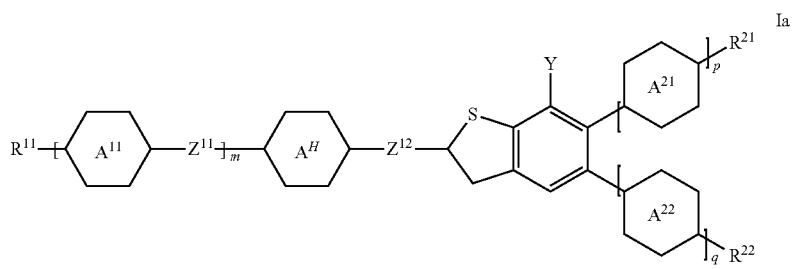

Ia in which $R^{11}$, $A^{11}$, $Z^{12}$, $R^{21}$, $R^{22}$, $A^{21}$ and $A^{22}$ are as defined in claim 1, and

is trans-1,4-cyclohexylene, 1,4-cyclohexenylene, or decaline-2,6-diyl, in which one or more non-adjacent CH$_2$ groups is optionally replaced by —O— and/or —S— and in which one or more H atoms is optionally replaced by F.

3. The compound of formula I according to claim 1, where the compound is selected a compound of the sub-formula Ib

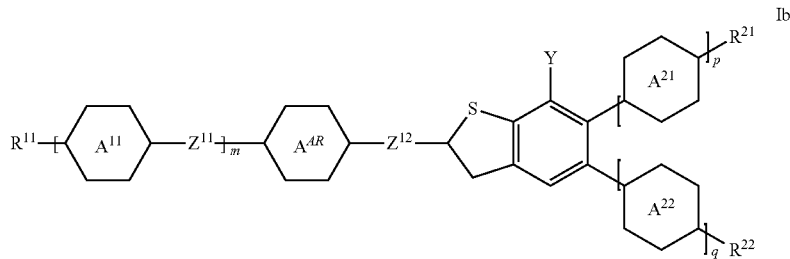

Ib in which $R^{11}$, $A^{11}$, $Z^{12}$, $R^{21}$, $R^{22}$, $A^{21}$ and $A^{22}$ are as defined in claim 1, and

is 1,4-phenylene or 2,6-naphthylene, in which one or two CH groups are optionally replaced by N and in which, in addition, one or more H atoms are optionally replaced by F, Cl or CF$_3$.

4. The compound of formula I according to claim 1, wherein $Z^{11}$ and $Z^{12}$ denote a single bond.

5. The compound of formula I according to claim 1, of the sub-formulae

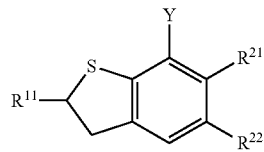

Ia-1

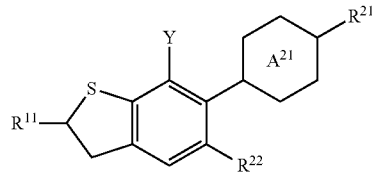

Ia-2

-continued

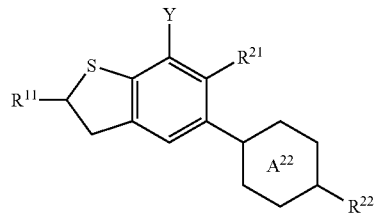

Ia-3

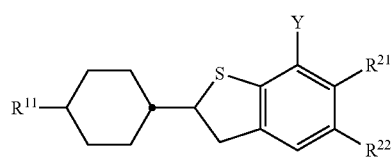

Ia-4

Ia-5
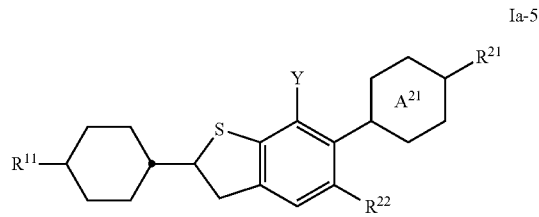
Ia-6
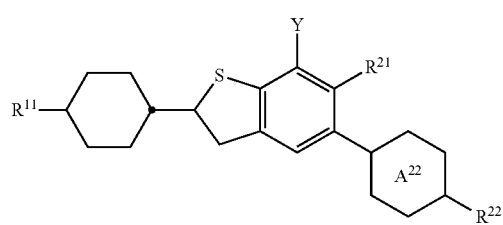
Ia-7
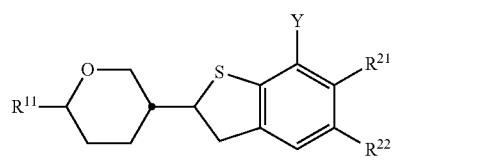
Ia-8
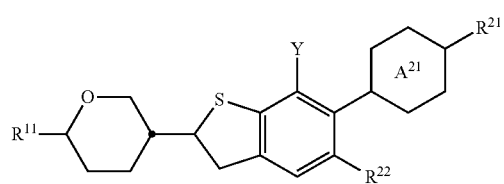
Ia-9
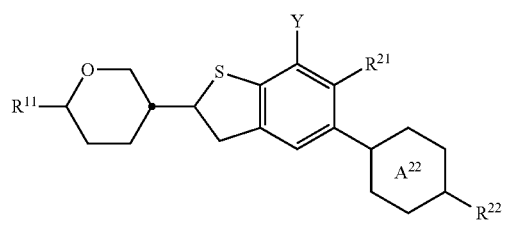
Ia-10
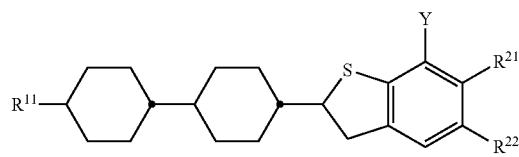
Ia-11
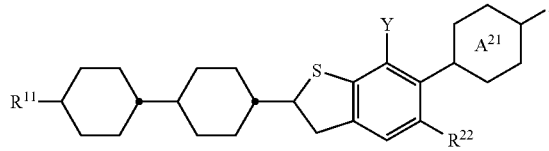
Ia-12
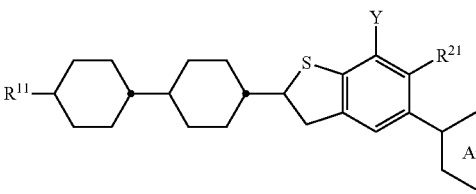
Ia-13
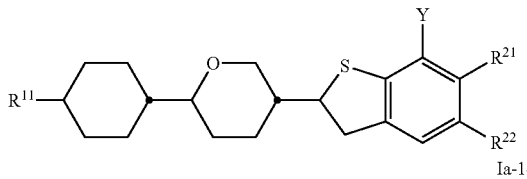
Ia-14
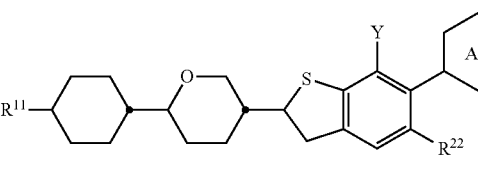
Ia-15
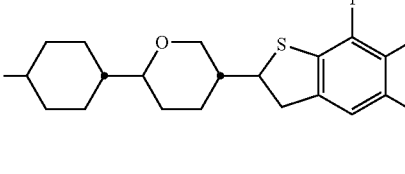
wherein $R^{11}$, $R^{21}$, $R^{22}$, Y, $A^{21}$ and $A^{22}$ have the meanings indicated in claim 1.
6. The compound of formula I according to claim 1, of the sub-formulae
Ib-1
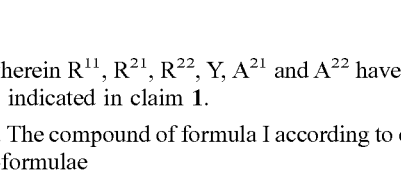
Ib-2
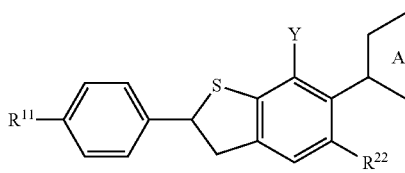
Ib-3
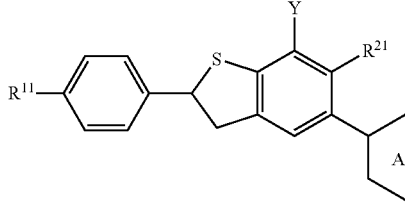

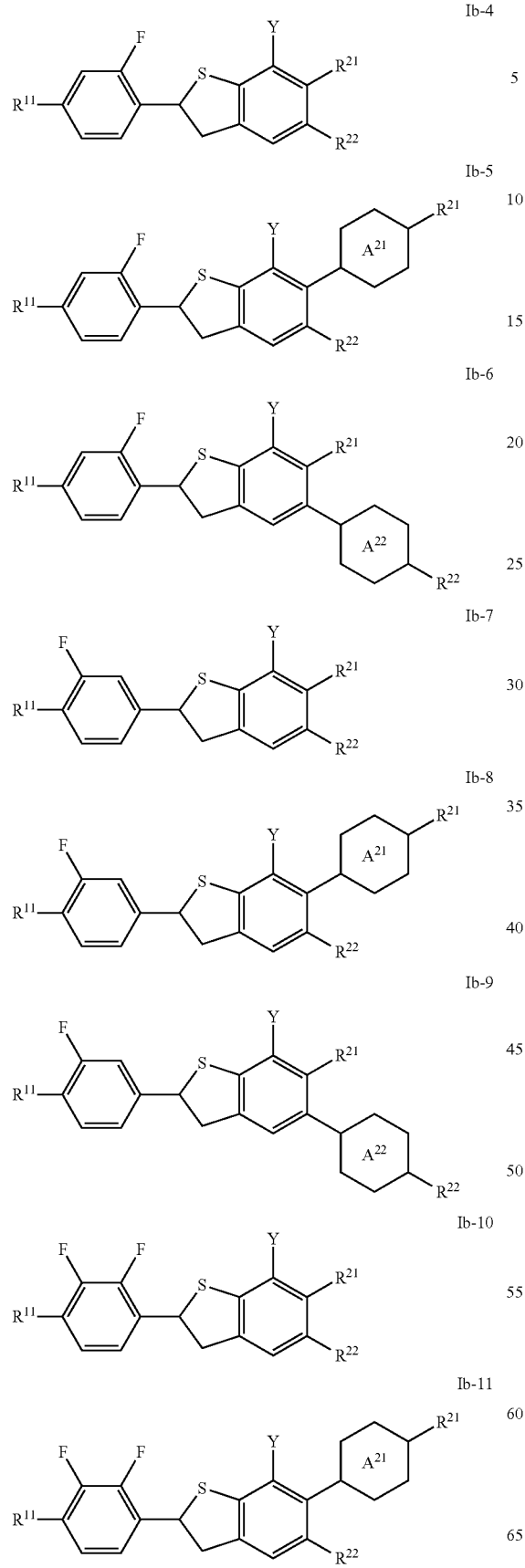
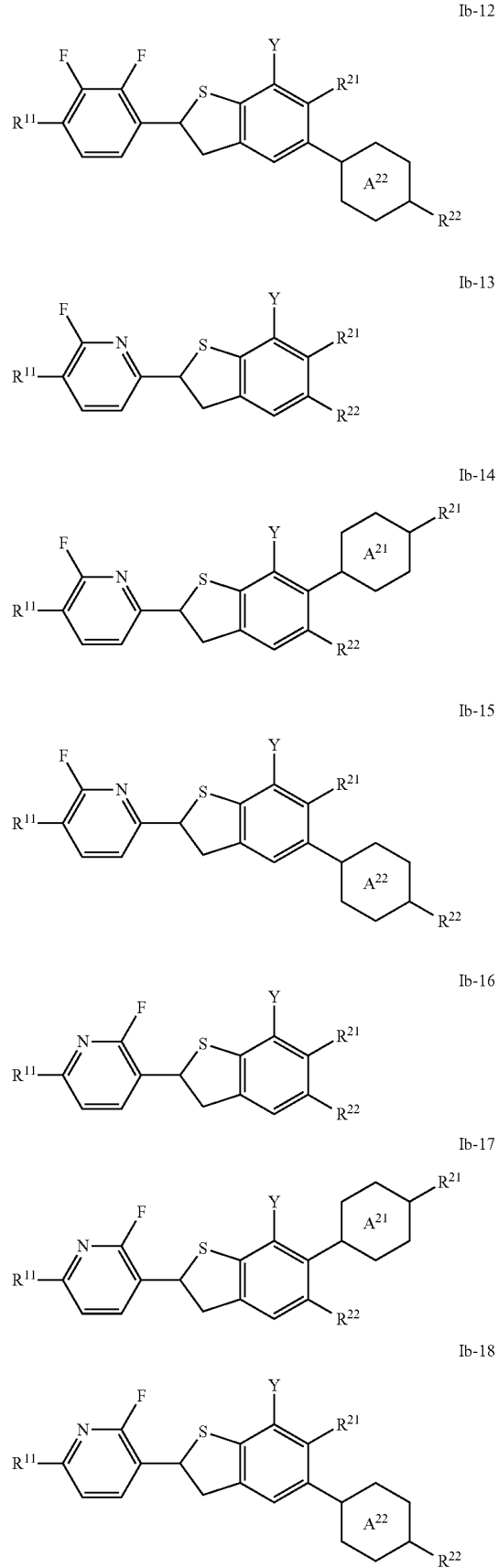

-continued
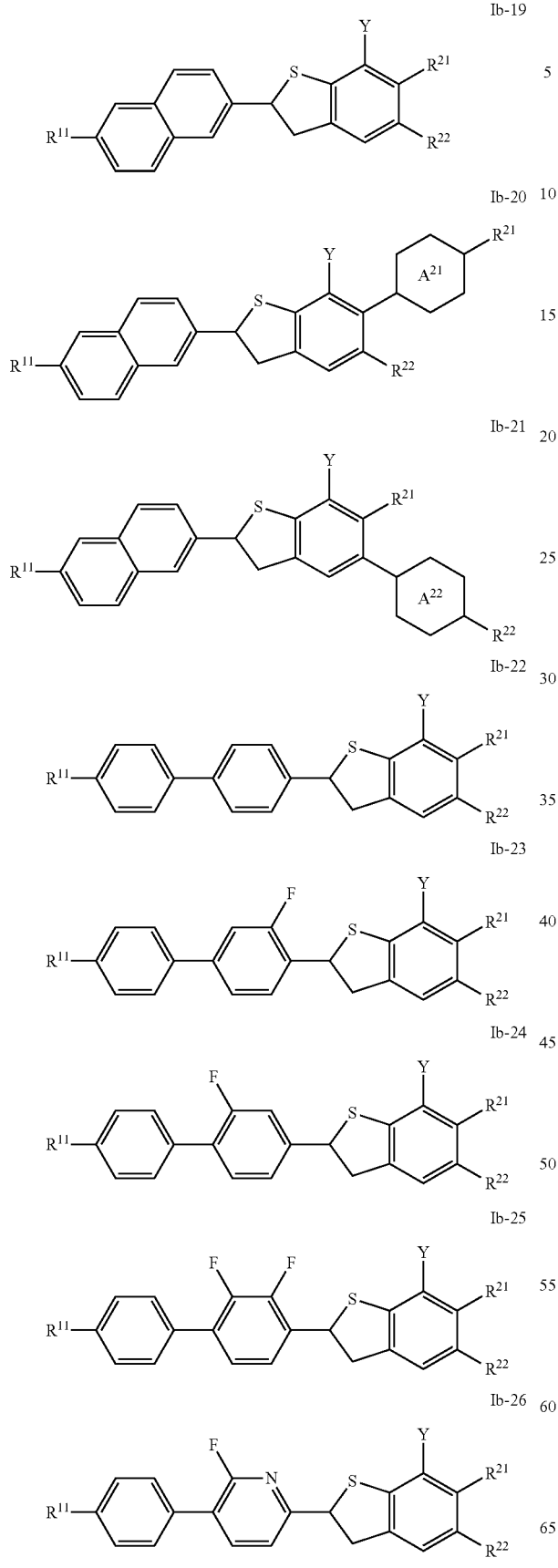
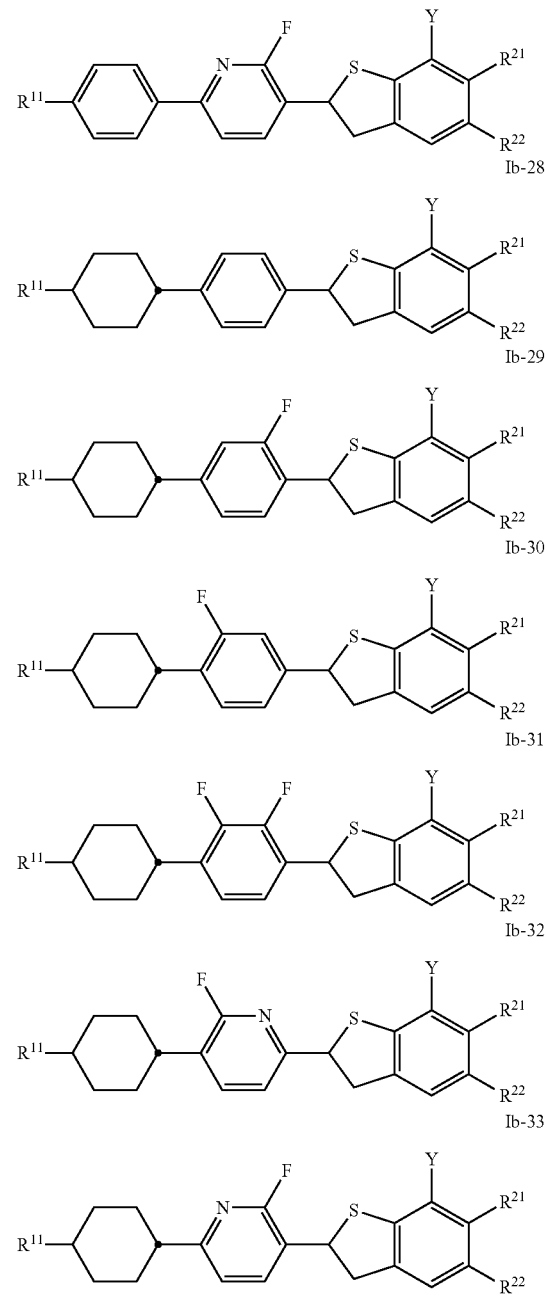
wherein $R^{11}$, $R^{21}$, $R^{22}$, Y, $A^{21}$ and $A^{22}$ have the meanings indicated in claim 1.
7. The compound of formula I according to claim 1 wherein
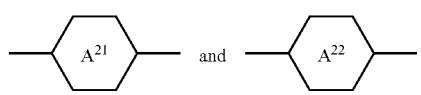
independently of one another, are 1,4-phenylene or 2,6-naphthylene, in which one or two CH groups are optionally replaced by N and in which, in addition, one or more H atoms may be replaced by F, Cl or $CF_3$.

8. The compound according to claim 1, wherein Y denotes F.

9. The compound according to claim 1, wherein $R^{11}$ denotes H, alkyl, alkenyl or alkoxy having up to 7 C atoms, and in which one or more H atoms is optionally replaced by fluorine, and $R^{21}$ and $R^{22}$, independently of one another, denote H, alkyl, alkenyl or alkoxy having up to 7 C atoms, F, Cl, CN, SCN, $SF_5$, $CF_3$, $OCF_3$, $OCF_2H$, $OCHF_2$, or —OCH=$CF_2$.

10. A process for the preparation of compounds of formula I according to claim 1, comprising hydrogenating in the presence of a catalyst a compound of formula II

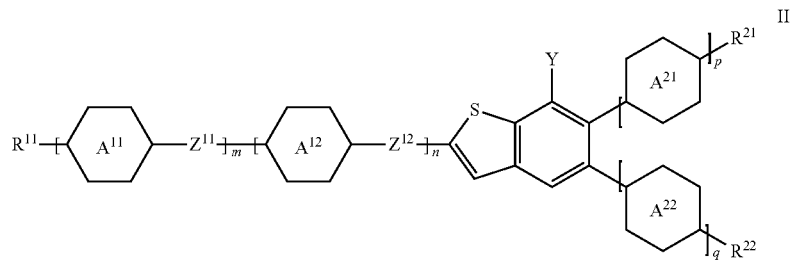

in which $R^{11}$, $A^{11}$, $Z^{12}$, $R^{21}$, $R^{22}$, $A^{21}$ and $A^{22}$ are as defined in claim 1.

11. A liquid-crystalline medium comprising two or more liquid-crystalline compounds, comprising one or more compounds according to claim 1.

12. An electro-optical display element containing a liquid-crystalline medium according to claim 11.

* * * * *